(12) United States Patent
Song

(10) Patent No.: US 7,781,211 B2
(45) Date of Patent: *Aug. 24, 2010

(54) ISOLATION OF MULTI-LINEAGE STEM CELLS

(75) Inventor: Sun U. Song, Incheon (KR)

(73) Assignee: Homeotherapy, Co. Ltd, Incheon (KR)

( * ) Notice: Subject to any disclaimer, the term of this patent is extended or adjusted under 35 U.S.C. 154(b) by 51 days.

This patent is subject to a terminal disclaimer.

(21) Appl. No.: 11/471,684

(22) Filed: Jun. 19, 2006

(65) Prior Publication Data

US 2006/0286669 A1  Dec. 21, 2006

Related U.S. Application Data

(60) Provisional application No. 60/595,254, filed on Jun. 17, 2005.

(51) Int. Cl.
*C12N 5/00* (2006.01)
*C12N 5/071* (2010.01)
*C12N 5/02* (2006.01)
*A01N 63/00* (2006.01)

(52) U.S. Cl. .................. 435/325; 435/372; 435/377; 424/93.1

(58) Field of Classification Search ................ 435/325, 435/372, 377; 424/93.1
See application file for complete search history.

(56) References Cited

U.S. PATENT DOCUMENTS 5,690,926 A     11/1997  Hogan
5,827,742 A *  10/1998  Scadden .................. 435/377
6,082,364 A *   7/2000  Balian et al. ............. 128/898

OTHER PUBLICATIONS

Shi et al. Blood 92:362-367; 1998.*
Woodbury et al. J. Neuroscience Res. 61:364-370; 2000.*
Gupta, C. Mol. Cell. Endocrinol. 152:169-178; 1999.*
Woodbury et al., "Adult Rat and Human Bone Marrow Stromal Cells Differentiate Into Neurons", Journal of Neuroscience Research (2000), 61:364-370.
Sato et al., "Human mesenchymal stem cells xenografted directly to rat liver are differentiated into human hepatocytes without fusion", Blood (2005), 106: 756-763.
Qu-Peterson et al., "Identification of a novel population of muscle stem cells in mice: Potential for muscle regeneration," The J. of Cell Biology, Rockefeller University Press, 157(5):851-864, May 27, 2002.
Lee et al., "Clonal isolation of muscle-derived cells capable of enhancing muscle regeneration and bone healing," The J. of Cell Biology, Rockefeller University Press, 150(5):1085-1099, Sep. 4, 2000.
Prockop et al., "Isolation and characterization of rapidly self-renewing stem cells from cultures of human marrow stromal cells," Cytotherapy, Isis Medical Media, 3(5):393-396, Jan. 1, 2001.
Colter et al., "Rapid expansion of recycling stem cells in cultures of plastic-adherent cells from human bone marrow," Proceedings of the National Academy of Sciences of USA, National Academy of Science, 97(7):3213-3218, Mar. 28, 2000.
Lu et al., "Can bone marrow-derived stem cells differentiate into functional neurons?" Experimental neurology, Academic Press, 193(2):273-278, Jun. 1, 2005.
Pittenger et al., "Multilineage potential of adult human mesenchymal stem cells," Science, 284(5411):143-147, Apr. 2. 1999.
Song et al., "Variations of clonal marrow stem cell lines established from human bone marrow in surface epitopes, differentiation potential, gene expression, and cytokine secretion," Stem Cells and Development, 17 (3):451-461, Jun. 2008.

* cited by examiner

*Primary Examiner*—Fereydoun G Sajjadi
(74) *Attorney, Agent, or Firm*—JHK Law; Joseph Hyosuk Kim

(57) ABSTRACT

The present application discloses a method of manipulating a biological sample of cells, which includes multi-lineage stem cells, progenitor cells, other marrow stromal cells: allowing the sample of cells to settle in a container; transferring supernatant from the container to another container; and isolating cells from the supernatant, which has comparatively lower density in the sample.

51 Claims, 17 Drawing Sheets

Isolated MLSC

HMSC 8292

CD 34

D5 (#2, FGF)

D4 (#3)

D5 (#2)

D4 (#1)

D5 (#1)

US 7,781,211 B2

ISOLATION OF MULTI-LINEAGE STEM CELLS

CROSS-REFERENCE To RELATED APPLICATIONS

The present patent application claims priority to U.S. Provisional Application No. 60/595,254, filed Jun. 17, 2005, the contents of which are incorporated by reference herein in their entirety.

BACKGROUND OF THE INVENTION

1. Field of the Invention

The present invention relates to the field of cell isolation. The present invention also relates to methods isolating various types of stem cells or progenitor cells.

2. General Background and State of the Art

Bone marrow is known to contain hematopoietic and mesenchymal stem and progenitor cells. Hematopoietic stem cells (HSCs) can generate various types of blood cells [1], and marrow stromal cells (MSCs) or mesenchymal stem cells are capable of differentiating into several different tissues including cartilage, bone and adipose [2,3,4]. MSCs were first found by Friedenstein and his colleagues [5] based on their adherence to cell culture dish. Undifferentiated MSC are fibroblast-like in morphology, self-renewable, and capable of differentiating into mainly connective tissues of the mesoderm origin, namely cartilage, bone, and fat. There are no certain cell surface proteins that specifically and uniquely identify MSCs yet. The diversity of characteristics associated with MSC can be explained by differences in tissue origin, isolation methods and culture conditions between laboratories [2,6,7,8]. Although there is no consistency, MSCs expanded in vitro express CD29, CD44, CD73, CD105, CD106, and CD166 [9], but lacks or are dimly positive for hematopoietic surface markers, such as CD11b, CD14, CD31, CD34, or CD45.

Cell populations with characteristics similar to MSC from different sources including mainly bone marrow, umbilical cord blood, and fatty tissue are known. Although it is difficult to identify whether these cells are distinct cell types due to lack of characteristic markers, they have some different level of surface marker expressions and various differentiation abilities, probably due to their distinct isolation and culture methods. The range of differentiation potential of MSCs is expanding, not only to mesoderm lineages but also to endoderm and/or ectoderm lineages. Therefore, the term "multi-lineage stem or progenitor cell (MLS/PC)" is suggested for these types of stem or progenitor cells capable of differentiating to mesoderm, ectoderm and/or endoderm lineages.

MSCs derived from adult bone marrow offer the potential to open a new strategy in medicine due to its ease of isolation and culture, stability of their phenotype in vitro and low or no allogeneic rejection. In fact, experimental evidence of the hypo-immunogenic nature of MSCs in humans and animals has been accumulating [10]. Currently, clinical applications of adult autologous or allogeneic MSCs have been conducted to treat a variety of diseases, and have generated very promising results [11].

Several protocols have been developed for isolation and expansion of MSCs in culture so far. These methods are based on using density-gradient centrifugation [12], FACs sorting [13,14], specific cell surface antibody [12,15,17,18], selective adhesion to laminin-coated plate [19], Hoechst dye exclusion, and size-sieved culture [24]. Potential disadvantages of these methods in terms of clinical applications are the heterogeneity of cultured cells, high risk of contamination, and/or high cost of production. Therefore, a new protocol to isolate highly homogeneous cell populations with less contamination potential and cost is desired for use in clinical settings.

The present application discloses a new isolation method developed to produce a highly homogeneous population of MLSCs with less contamination potential and cost for clinical applications. This method does not necessarily utilize density-gradient centrifugation, antibody selection, or FACS sorting, but preferably uses mainly natural gravity in a non-coated, collagen or polylysine-coated culture dishes and sub-fractionation cell culture to separate adherent bone marrow cells according to their cell density. Several distinct highly homogeneous populations of MLSC lines derived from single-cell derived colonies were isolated and expanded with this protocol from human bone marrow. These stem cell lines are self-renewable and capable of differentiating into several different lineages, such as chondrogenic, osteogenic, adipogenic, neurogenic, and hepatogenic lineages.

SUMMARY OF THE INVENTION

The invention provides adult stem or progenitor cells that can be used to treat diseases, such as graft versus host disease, osteoarthritis, rheumatoid arthritis, osteogenesis imperfecta and others and to repair tissues, such as skin, cartilage, bone, muscle and nerve.

The invention is directed to a method of manipulating a biological sample of cells, comprising: (i) allowing the sample of cells to settle in a container; (ii) transferring supernatant from the container to another container; and (iii) isolating cells from the supernatant, which has comparatively lower density in the sample.

The sample of cells may be mixed with a growth medium. Further, in the above method, the steps (i) and (ii) are carried out at least three times, and the isolated cells from the supernatant may be expanded in a container. The container may have a flat bottom, and may be coated with a cell adhesive agent. The cell adhesive agent may be a positively or negatively charged molecule(s). Preferably the cell adhesive agent may be collagen, polylysine, or other charged amino acids, such as polyarginine, polyaspartate, polyglutamate or a combination thereof. The sample of cells may be obtained from bone marrow, peripheral blood, cord blood, fatty tissue sample, or cytokine-activated peripheral blood, and a single colony of multi-lineage stem cells or progenitor cells may be isolated.

In one aspect, the invention is concerned with isolating multi-lineage stem cells. The cells may be progenitor cells.

In one embodiment, the isolation method may exclude centrifugation step of the sample of cells. In another embodiment, the biological sample of cells may be obtained prior to undergoing any centrifugation. Yet in another embodiment, the biological sample of cells may be obtained after undergoing centrifugation, preferably mononuclear cells isolated or fractionated by conventional density-gradient centrifugation method typically employed for MSC isolation.

In another aspect, the invention is directed to a method of making endodermal, mesodermal, or ectodermal cell lineage by contacting the appropriate inducing or transforming/differentiating medium with the isolated multi-lineage stem cells obtained by using the preparation method as described herein.

These and other objects of the invention will be more fully understood from the following description of the invention, the referenced drawings attached hereto and the claims appended hereto.

BRIEF DESCRIPTION OF THE DRAWINGS

The present invention will become more fully understood from the detailed description given herein below, and the accompanying drawings which are given by way of illustration only, and thus are not limitative of the present invention, and wherein.

DETAILED DESCRIPTION OF THE PREFERRED EMBODIMENTS

Figure 1:
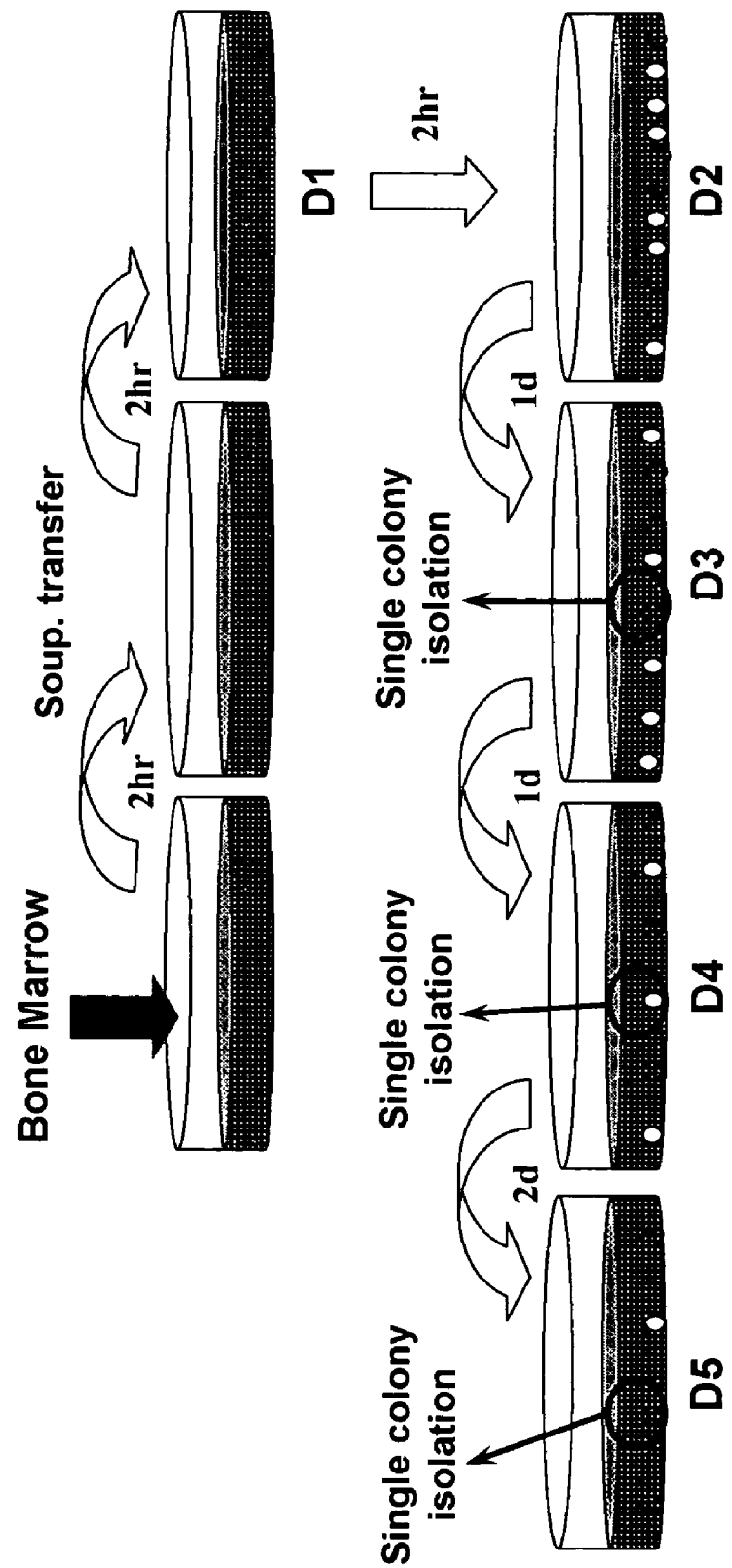
FIG. 1 shows overall flow diagram for the isolation of multi-lineage stem cells from human bone marrow using a subfractionation culturing method. In brief, 1 ml of human bone marrow was mixed with 15 ml of DMEM-HG, DMEM-LG, or a-MEM (20% FBS) and plated onto 10 cm$^2$ cell culture dish. After 2 hour incubation, only supernatant was transferred to a new dish. This was repeated once more. The supernatant was then transferred to a non-coated, collagen- or polylysine-coated dish. From this stage, the cells were incubated for 1 day twice and 2 days once. The final supernatant was incubated until single clones of cells appeared. When single clones of cells were big enough to transfer to 6-well plate, the cells were expanded to larger plates for further studies.

In the present application, "a" and "an" are used to refer to both single and a plurality of objects.

As used herein, "bodily sample" refers to any sample obtained from a mammal from which is desired to isolate a single type of cell. Such bodily sample includes bone marrow sample, peripheral blood, cord blood, fatty tissue sample, and cytokine-activated peripheral blood.

As used herein, "sample of cells" refers to any sample in which is contained a mixture of different types of cells, including bone marrow sample, peripheral blood, cord blood, fatty tissue sample, and cytokine-activated peripheral blood.

As used herein, "homogeneous" population of cells generally indicates that the same type of cells are present within the population Substantially homogeneous may mean about 80% homogeneity, or about 85%, 90%, 91%, 92%, 93%, 94%, 95%, 96%, 97%, 98%, 99% 99.1%, 99.2%, 99.3%, 99.4%, 99.5%, 99.6%, 99.7%, 99.8%, or 99.9% homogeneity.

As used herein, "lower density cell" refers to cells that have lower density than others in the sample, and are the object of isolation. The lower density cell includes without limitation, multi-lineage stem cells, progenitor cells, other marrow stromal cells.

As used herein, "MLSC" refers to multi-lineage stem cell.

As used herein, "MLSC/PC" refers to multi-lineage stem cell or progenitor cell.

As used herein, "MSC" refers to marrow stromal cells or mesenchymal stem cells, which terms are used interchangeably.

Subfractionation Technique

The present application describes a new method, named subfractionation culturing method, that isolates a highly homogeneous population of multi-lineage stem cells (MLSCs) from a bodily sample or source such as human bone marrow. A total of sixteen bone marrow cell lines were established out of one ml of bone marrow aspirate. Of the sixteen, four cell lines showing distinct phenotypes by FACS analysis were further characterized. All of these cell lines showed characteristics of multi-lineage stem cells, such as the self-renewal ability and the capacity of differentiating into mesoderm, ectoderm, and endoderm lineage cells.

Bone marrow MSCs have been known to be difficult to isolate without contamination by hematopoietic cells [20, 21]. For application in clinical settings, it is important to have a homogeneous population of MSCs in order to prevent immunogenic problems and to evaluate the clinical effects correctly. Conventionally, isolation of homogeneous populations of MSCs was carried out by MSC-specific antibody column purification. However, even this method is not adequate as no such perfect MSC-specific antibody is available yet.

A rationale for the inventive method for isolating MLSCs from a biological sample such as a bone marrow sample is that multi-lineage stem or progenitor cells have low cell density and therefore they can be separated from other cells in the sample on this basis. For example, mature MSCs are larger than rapidly self-renewing (RS) cells [22, 23]. RS cells are known to possess a greater capacity for multi-lineage differentiation.

In another aspect, collagen or polylysine-coated culture dishes were used in order to obtain more adherent stem cells.

Applicant has discovered that any charged culture surface, either positive or negative, helps the attachment of stem cells to it, compared to the surface of a non-coated dish. More cells were attached to a collagen or polylysine-coated culture dish than a non-coated dish, approximately about two to three fold respectively (data not shown). Similar results were obtained with other human bone marrow aspirates and three different strains of mouse bone marrow samples in terms of obtaining of single-cell derived marrow cell colonies (data not shown), indicating that this protocol is consistent with other bone marrow aspirates and can be applied to isolate MLSCs in other species as well.

Thus, in one embodiment, the bottom of a culture dish can be coated by either positively charged amino acids, such as polylysine, polyarginine, or negatively charged amino acids, such as polyaspartate, polyglutamate, or a combination thereof to help stem or progenitor cells adhere better to the bottom of the dish.

To practice the inventive subfractionation culturing method, it is not necessary to employ centrifugation of any type to pre-remove any type of cells such as red or white blood cells from the sample because most of the heavier or more dense cells can be removed within the first two, 2-hour incubation steps. Thus, one advantage of the inventive system is that conventionally used gradient centrifugation and mononuclear cell fractionation steps, which may introduce contamination such as Picoll, Ficoll or Ficoll-hypaque into the cell culture may be avoided. Accordingly, the inventive subfractionation culturing method is a simple, effective, and economic protocol to isolate highly homogeneous MLSCs from a bodily sample, preferably a bone marrow sample.

Alternatively, mononuclear cells isolated/fractionated by conventional density-gradient centrifugation method of MSC isolation can also be subjected into the D1 dish to obtain single cell-derived colonies and then to isolate homogeneous populations of stem or progenitor cells. Therefore the fractionation culturing method can be used with the mononuclear cells fractionated by the conventional density-gradient centrifugation.

The present application describes diversity of characteristics in cell surface protein expression of the isolated single-cell derived stem cell lines, which indicates that there are several different types of multi-lineage stem or progenitor cells that exist in biological samples, and in particular bone marrow samples, which are exemplified. The isolated MLSCs were generally negative or dimly positive for CD34, HLA-DR, CD73, CD31, CD166, HLA Class I and highly positive for CD44, CD29, CD105. However, some cell lines from D4 and D5 dishes exhibited distinctive levels of surface proteins, which indicates that there could be several different types of multi-lineage stem or progenitor cells in bone marrow. Hung et al. also speculated that bone marrow may include many groups of MSCs that are different in surface marker analyses [24]. These MSCs having different surface markers may represent different differentiation potential of the cells. Therefore, isolation of single-cell derived homogeneous stem cells by the inventive subfractionation culturing method makes it possible to isolate tissue-specific stem or committed progenitor cells, as long as these groups of cells exist in the bone marrow or other specifically isolated bodily sample, and culture conditions do not change their potential during cell expansion. The safety and efficacy of MSC treatment and cell engraftment process is improved by being able to characterize subpopulations of cells with specific properties, as shown in the present application.

The present application shows a novel method that isolates a highly homogeneous population of MLSC lines derived from single cells from any other bodily sample, bone marrow cells in particular, with the capacity of renewal and multi-lineage differentiation into ectoderm, mesoderm, and endoderm lineage cells. By eliminating density-gradient centrifugation and mononuclear cell fractionation steps and without requiring the use of antibodies to separate stem cells, the inventive subfractionation culturing method generates more homogeneous populations of MLSCs in a simple, effective, and economic procedure and safer applications for therapeutic settings.

Induction, Differentiation/Transformation Agents for Endoderm Cell Lineage

Induction, differentiation/transformation agents for endoderm cell lineage include the following agents: hepatocyte growth factor, oncostatin-M, epidermal growth factor, fibroblast growth factor-4, basic-fibroblast growth factor, insulin, transferrin, selenius acid, BSA, linoleic acid, ascorbate 2-phosphate, VEGF, and dexamethasone, for the following cell types: liver, lung, pancreas, thyroid, and intestine cells.

Induction, Differentiation/Transformation Agents for Mesoderm Cell Lineage

Induction, differentiation/transformation agents for mesoderm cell lineage include the following agents: insulin, transferrin, selenous acid, BSA, linoleic acid, TGF-β1, TGF-β3, ascorbate 2-phosphate, dexamethasone, β-glycerophosphate, ascorbate 2-phosphate, BMP, and indomethacine, for the following cell types: cartilage, bone, adipose, muscle, and blood cells.

Induction, Differentiation/Transformation Agents for Ectoderm Cell Lineage

Induction, differentiation/transformation agents for ectoderm cell lineage include the following agents: dibutyryl cyclin AMP, isobutyl methylxanthine, human epidermal growth factor, basic fibroblast growth factor, fibroblast growth factor-8, brain-derived neurotrophic factor, and/or other neurotrophic growth factor, for the following cell types: neural, skin, brain, and eye cells.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims. The following examples are offered by way of illustration of the present invention, and not by way of limitation.

EXAMPLES

Example 1

Isolation of MLSCs and Cell Culture

One-ml of discarded human bone marrow aspirate, taken from the iliac crest of a patient undergoing bone marrow examination after informed consent and approval of the Inha University Medical School IRB, were mixed with 15 ml of complete growth medium: Dulbecco's modified Eagle's Medium (DMEM) containing high or low glucose (GIBCO-BRL, Life-technologies, MD USA), with 20% fetal bovine serum (FBS) and 1% penicillin/streptomycin, and then incubated in 100 mm culture dish. As shown in FIG. 1, after 2 hour incubation at 37° C., 5% $CO_2$, only the cell culture supernatant was transferred to a new dish. After another 2 hour incubation in a new dish, the supernatant was transferred to a non-coated, collagen or polylysine-coated dish and incubated for 2 hours (D1). After transferring the supernatant one more time to a new dish (D2), the supernatant was transferred to a new dish and then incubated for 1 day (D3). This was repeated two more times with 1 and 2 day incubation (D4 and D5 respectively). The single colonies grown in the D4 or D5 dish were transferred to a 100 mm plate first and then kept expanded in larger culture flasks. After usually 10 to 14 days in the 100 mm plate, the cells were harvested with 0.25% trypsin and 1 mM EDTA (GIBCO-BRL), suspended at $1 \times 10^6$ cells/ml in 10% dimethylsulfoxide (DMSO) and 40% FBS, and frozen in 1 ml aliquots in liquid nitrogen (passage 1). For detaching and isolating of single colonies, trypsin/EDTA was used for 1-2 minutes with a sterile cylinder. Once the cells reached about 80 to 90% confluence, they were recovered with trypsin/EDTA and replated at 50-100 cells/cm$^2$.

Example 2

Flow Cytometry Analysis

The isolated and expanded cells from single-cell derived colonies were characterized at passage 3 or 4 by flow cytometric analysis for a panel of cell surface proteins. The cells were harvested from 75 cm$^2$ flask by treatment of trypsin/EDTA and washed with PBS twice. The cells were incubated in PBS with 0.1% goat serum for blocking and then washed with washing buffer (PBS with 0.4% BSA) twice. The cells were incubated with fluorescein isothiocyanate (FITC) or phycoerythrin (PE)-conjugated antibodies for 40 min at 4° C. Tested antigens included matrix receptors (CD13, CD44, CD105), integrin (CD29), PECAM (CD31), ALCAM (CD166), SH3 and SH4 (CD73), Thy-1 (CD90) and hematopoietic lineage markers (CD34, HLA-DR, HLA-ClassI) (BD Biosciences Pharmingen, San Diego, Calif., USA). The cell mixture was then washed twice with washing buffer and analyzed using a fluorescence-activated cell sorter (FACS) with a 525 nm filter for green FITC fluorescence and with a 575 nm filter for red PE fluorescence. As a control, human mesenchymal stem cells (HMSC 8292, Cambrex Bio Science, Walkersville, Md. USA) were used.

Example 3

Induction of Multi-Lineage Differentiation

Pellet culture assay was used for chondrogenic, osteogenic, adipogenic differentiation experiments using passage 3 or 4 cells. $2 \times 10^5$ cells in 0.5 ml culture medium were spun down to make a pellet. The following supplements in DMEM containing high glucose and 20% FBS were used for each lineage, chondrogenic differentiation medium: 6.25 µg/ml insulin (Sigma Chemical Co, St Louis, Mo., USA), transferrin (Sigma), 6.25 ng/ml selenous acid (Sigma), 1.25 mg/ml BSA (Sigma), 5.35 µg/ml linoleic acid (Sigma), TGF-β1 10 ng/ml (R&D Systems, Minneapolis, Minn., USA), and TGF-β3 10 ng/ml (R&D Systems, Minneapolis, Minn., USA); osteogenic differentiation medium: 50 µg/ml ascorbate 2-phosphate (Sigma), $10^{-8}$ M dexamethasone (Sigma), and 10 mM β-glycerophosphate (Sigma); adipogenic differentiation medium: 50 µg/ml ascorbate 2-phosphate (Sigma), $10^{-7}$ M dexamethasone (Sigma), and 50 µg/ml indomethacine (Sigma). The pellet culture was incubated at 37° C., 5% CO$_2$ and medium was changed every 3 days.

For neurogenic differentiation, the isolated and expanded cells at passage 3 were seeded into a 6 well culture plate at a concentration of $1 \times 10^4$ cells with basic medium. After 24 hours, the basic medium was discarded and replaced by neuronal differentiation medium. The cells were cultured 1 mM dibutyryl cyclin AMP (dbcAMP; Sigma, St. Louis, Mo.), 0.5 mM isobutyl methylxanthine (IBMX; Sigma, St. Louis, Mo.), 20 ng/ml human epidermal growth factor (hEGF; Sigma, St. Louis, Mo.), 40 ng/ml basic fibroblast growth factor (bFGF; Sigma, St. Louis, Mo.), 10 ng/ml fibroblast growth factor-8 (FGF-8; PEPROTECH INC, Rocky Hill, N.J.), 10 ng/ml brain-derived neurotrophic factor (BDNF; R&D Systems, Minneapolis, Minn.). NEUROBASAL™ media (GIBCO BRL, Gaithersburg, Md.) with 1×B27 supplement (GIBCO BRL, Gaithersburg, Md.) is a serum-free basal medium for the long-term viability of hippocampal and other neurons of the central nervous systems.

For hepatocyte differentiation, the isolated and expanded cells at passage 4 were plated at a concentration $1 \times 10^4$ cells into 60 mm dish. After 24 hours, the cells were treated with differentiation medium containing 20 mg/ml hepatocyte growth factor (R&D), 10 ng/ml oncostatin-M (R&D), 10 ng/ml epidermal growth factor (sigma), 20 ng/ml fibroblast growth factor-4 (R&D), 10 ng/ml basic-fibroblast growth factor (sigma), 50 mg/ml ITS+premix (Becton Dickinson; 6.25 µg/ml insulin, 6.25 µg/ml transferrin, 6.25 ng/ml selenius acid, 1.25 mg/ml BSA, 5.35 mg/ml linoleic acid)), 0.1 µM ascorbate 2-phosphate (sigma), $10^{-8}$M dexamethasone (sigma). Medium was changed every 3 days.

Example 4

Histochemical and Immunohistochemical Staining

Histochemical staining and immunohistochemistry study were performed 14 or 21 days after the initiation of differentiation culture. The pellets were washed with PBS twice after removing the differentiation medium. The pellets were embedded with OCT compound (Sakura Finetek, Torrance, Calif., USA) and 6 µm sections were stained. The tissues were stained with toluidine blue, von Kossa, and Oil red-O to show chondrogenic, osteogenic, and adipogenic differentiation respectively. Immunohistochemical staining for human type II collagen was also performed to demonstrate chondrogenic differentiation of the tissue.

For the immunocytochemical staining of neuronal cells, all wells were then fixed with 99.9% ethanol and labeled with mouse anti-neuronal nuclear antigen (NeuN, 10 ug/ml) IgG monoclonal antibody (Chemicon, Temecula, Calif.), mouse anti-nestin (5 ug/ml) IgG monoclonal antibody (Chemicon, Temecula, Calif.) and monoclonal anti-Glial Fibrillary Acidic Protein (GFAP, 1:400; Sigma, St. Louis, Mo.) for 1 hour at room temperature. The cells were then rinsed with PBS, and immunostaining was detected using the Histostain-Plus Kit (Zymed Laboratories Inc., San Francisco, Calif.). DAB served as the chromogen. Cells were photographed with a digital camera to assess the positive expression of neuronal specific markers.

Example 5

RNA Extraction and RT-PCR analysis

Total RNA was extracted from the non-differentiated and differentiated cells using TRIZOL® (Invitrogen Co, Carlsbad, Calif., USA) reagent. Complementary DNA was synthesized with total RNA (1 µg using Reverse Transcription System Kit (Promega). PCR was performed using specific primers designed for each lineage as follows: col-2 (500 bp), sense: 5'-AAGATGGTCCCAAAGGTGCTCG-3' (SS101-F SEQ ID NO:1) and antisense: 5'-AGCTTCTCCTCT- GTCTCCTTGC-3' (SS101-R SEQ ID NO:2); osteopontin (330 bp), sense: 5'-CTAGGCATCACCTGTGCCATACC-3' (SS102-F SEQ ID NO:3) and antisense: 5'-CGTGACCAGT-TCATCAGATTCATC-3' (SS102-R SEQ ID NO:4), PPAR-γ2 (352 bp), sense: 5'-GCTGTTATGGGTGAAACTCTG-3' (SS103-F SEQ ID NO:5) and antisense: 5'-ATAAGGTG-GAGATGCAGGCTC-3' (SS103-R SEQ ID NO:6), GAPDH (350 bp), sense: 5'-AACTCCCTCAAGATTGTCAGCA-3' (SS104-F SEQ ID NO:7) and antisense: 5'-TCCACCAC-CCTGTTGCTTGTA-3' (SS104-R SEQ ID NO:8), NF-M (430 bp), sense: 5'-GAG CGCAAAGACTACCTGAAGA-3' (SS105-F SEQ ID NO:9) and antisense: 5'-CAGCGATTTC-TATATCCAGAGCC-3' (SS105-R SEQ ID NO:10), and αFP (216 bp), sense: 5'-TGCAGCCAAAGTGAAGAGG-GAAGA-3' (SS106-F SEQ ID NO:11) and antisense: 5'-CAT-AGCGAGCAGCCCAAAGAAGAA-3' (SS106-R SEQ ID NO:12). PCR was performed for 35 cycles with each cycle of denaturing at 95° C. for 1 min, annealing at 56° C. for 1 min, and elongating at 72° C. for 1 min. The amplified DNA products were run on a 1% agarose gel.

Example 6

Results

Example 6.1

Isolation and Expansion of Bone Marrow Cell Colonies

In order to explore if it is possible to isolate human bone marrow stem or progenitor cells by subfractionstion culturing method, as described in FIG. 1, bone marrow was mixed with culture medium and kept fractionated by transferring only the cell culture supernatant to new dishes. The rationale of this fractionation is based on the hypothesis that bone marrow stem or progenitor cells may have low cell density. It was usually not possible to obtain well-separated single colonies in D1 and D2 dishes. There were at least few different types of cells observed with distinct morphology and size in D1 and D2 dishes, indicating the cellular heterogeneity in marrow-derived adherent monolayer cultures. The adherent cells in D1 or D2 culture dish reached confluence at 7 to 10 or 14 to 21 days respectively after transferring cell culture supernatant from the previous dish. It became possible to obtain well-separated single-cell derived colonies in D3, D4, and D5 dishes. The initial adherent spindle-shaped cells appeared as single colonies between 14 to 21 days after transferring culture supernatant from the previous dish. Ten, three, and three single-cell derived colonies appeared in D3, D4, or D5 dish respectively.

Figure 2:
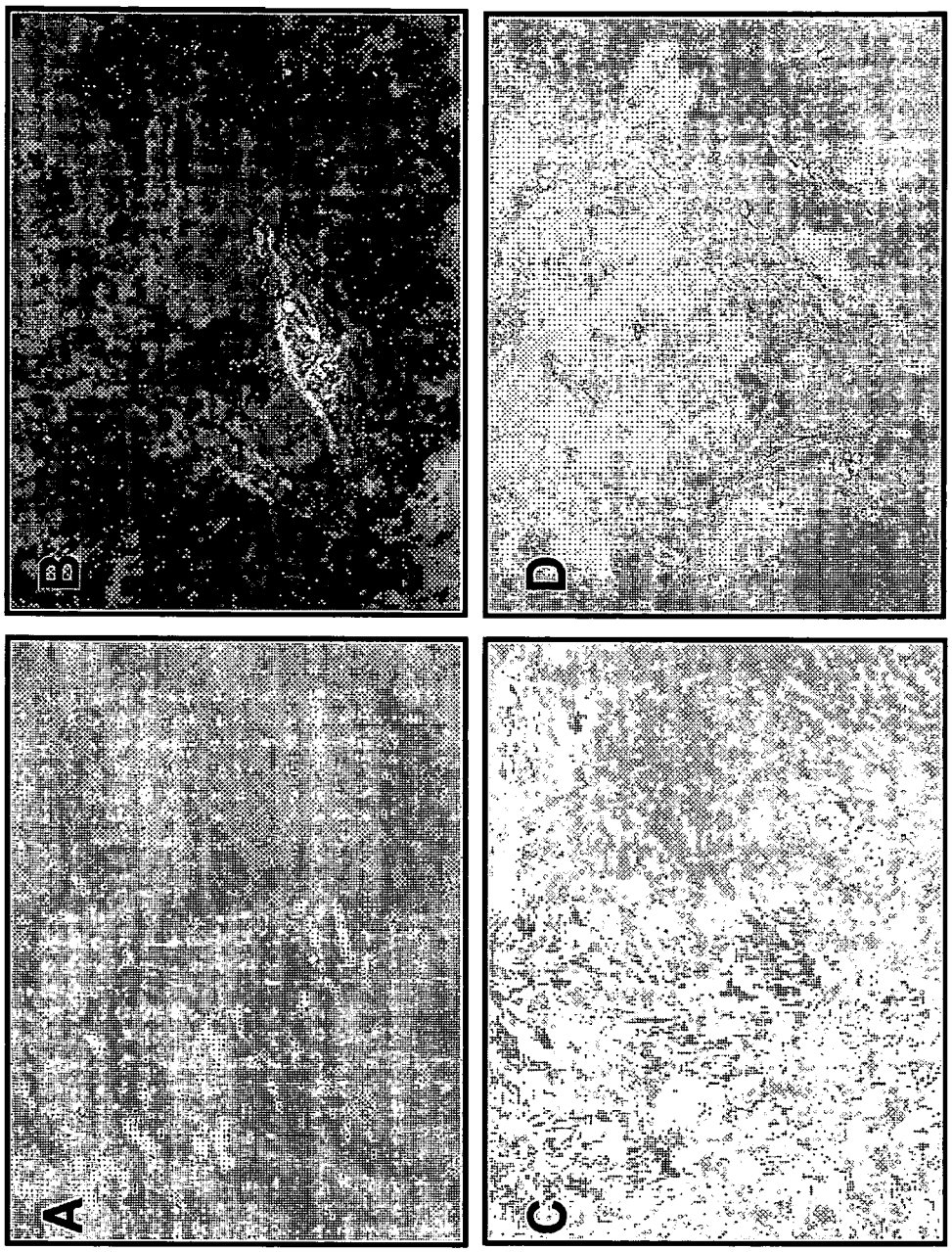
FIGS. 2A-2D show the morphological characteristics of isolated multi-lineage stem cells from bone marrow. (A & B) MLSCs three days after the final subfractionation of bone marrow cells. Cells have fibroblast-like morphology. Magnification: (A) 40× and (B) 200×. (C) Cells reached confluence with a consistent and homogeneous morphology at day seven. (D) After six passages of the isolated MLSCs, the morphology of a small portion (less than 2 to 3%) of MLSCs was changed to a wider and larger shape, compared to the ones at earlier passages. The morphology of the isolated and expanded MLSCs is spindle shape which is similar to known marrow stromal stem cells.
Figure 3:
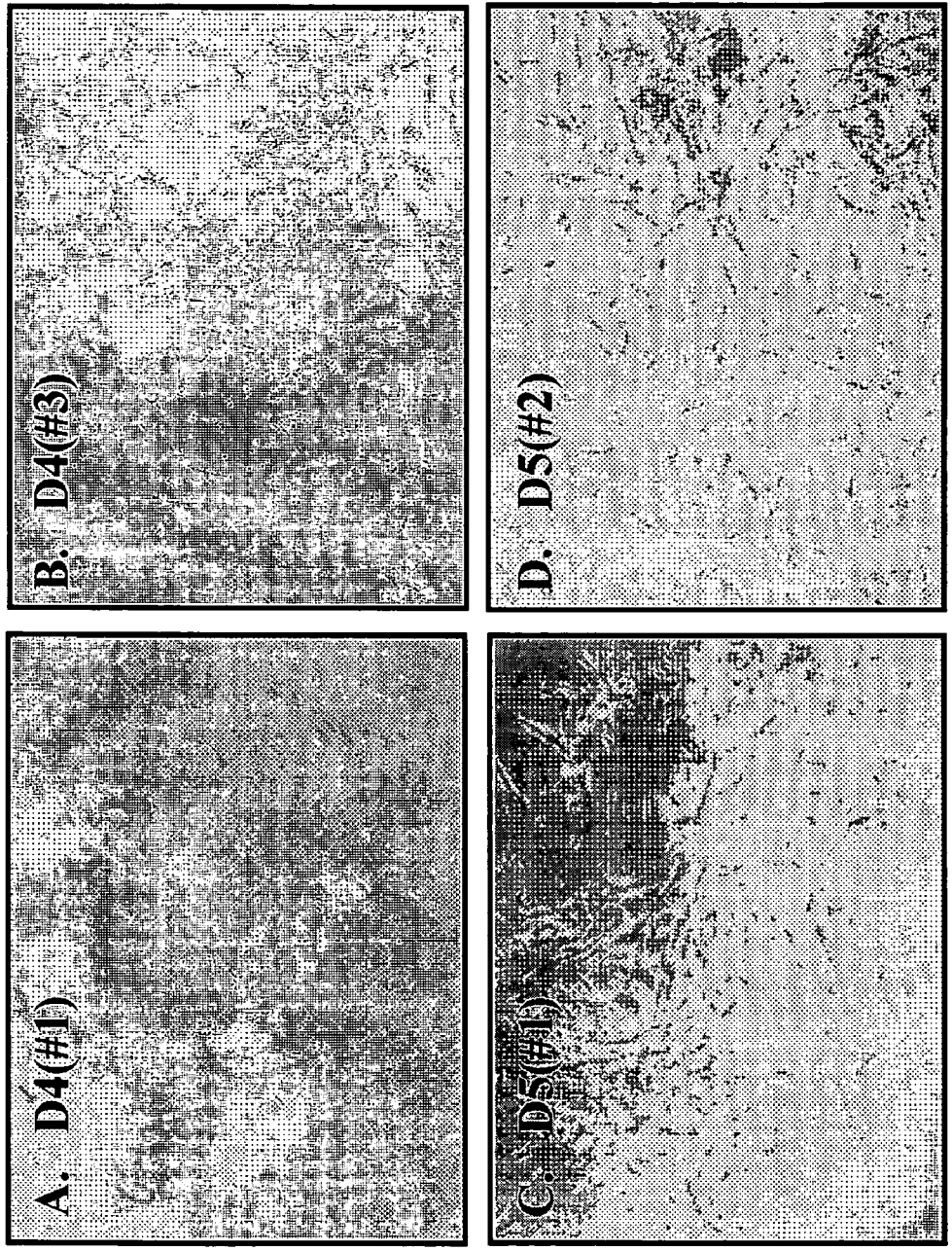
FIGS. 3A-3D show the morphology of four established multi-lineage stem cell lines from bone marrow. Pictures of four established multi-lineage stem cell lines, called A. D4(#1), B. D4(#3), C. D5(#1), and D. D5(#2), grown to about 70 to 80% confluence. The morphology of the established multi-lineage stem cell lines is spindle shaped and these stem cells grow as fast as other fibroblast cells.

FIG. 2 shows the morphological characteristics of isolated multi-lineage stem cells from bone marrow three days after the final subfractionation of bone marrow cells. The cells have fibroblast-like morphology. The cells reached confluence with a consistent and homogeneous morphology at day seven. After six passages of the isolated MLSCs, the morphology of a small portion (less than 2 to 3%) of MLSCs was changed to a wider and larger shape, compared to the ones at earlier passages. The morphology of the isolated and expanded MLSCs is spindle shape which is similar to known marrow stromal stem cells. Once the colonies of approximately 200 to 300 cells were formed, the cells proliferated rapidly as fast as normal fibroblast cells do. Among the six cell lines generated from the individual colonies in D4 and D5 dishes, four cell lines showed distinct phenotypes by FACS analysis and were further characterized. These cell lines at 70-80% confluence in culture dishes are shown in FIG. 3.

Example 6.2

Phenotypic Characterization of Bone Marrow Cell Lines

To characterize the phenotypes of single-cell derived bone marrow cell lines, a panel of cell surface proteins was analyzed by FACS analysis, as summarized in Table 1.

TABLE 1

Summary of cell surface protein expression of the isolated MLSC lines assayed by FACS analysis

| Cell Surface Protein | D4 (#1) | D4 (#3) | D5 (#1) | D5 (#2) | D5 (#2, FGF) |
|---|---|---|---|---|---|
| CD13 | L | L | N | L | L |
| CD29 | H | H | I | H | H |
| CD31 | L | L | N | N | I |
| CD34 | L | L | N | L | L |
| CD44 | H | H | H | H | H |
| CD73 | L | L | N | L | I |
| CD90 | H | H | H | H | I |
| CD105 | H | H | I | H | H |
| CD166 | H | H | I | H | H |
| HLA-DR | N | L | N | N | L |
| HLA-ClassI | H | H | I | H | H |

(N—negative, L—low, I—intermediate, H—high)

Figure 4:
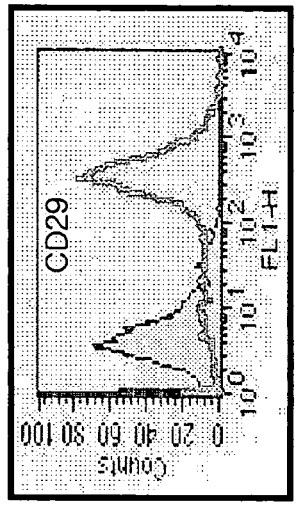
FIG. 4 shows the cell surface proteins of isolated MLSCs from bone marrow by a subfractionation culturing method. Flow cytometry analyses showed that MLSCs were consistently positive for typical MSC integrin protein (CD29) and matrix receptors (CD44 and CD105). HMSC8292 (Cambrex Bio Science, Walkersville, Md., USA) cells were used as a control. The cell surface proteins which are known to be expressed for typical MSC are also expressed in MLSCs, suggesting that MLSCs could have MSC characteristics.
Figure 4:
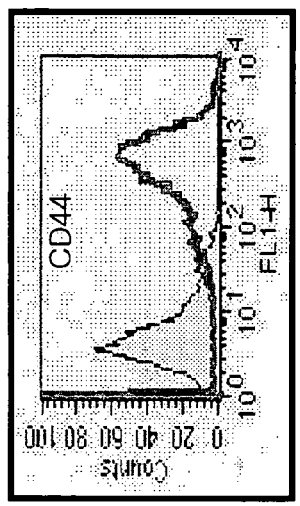
Figure 4:
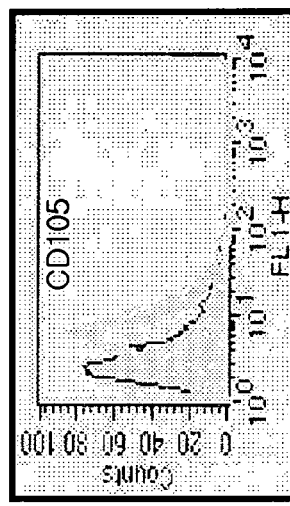
Figure 4:
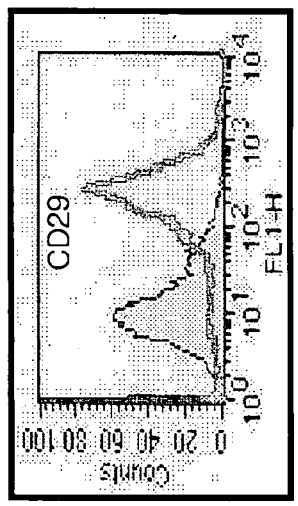
Figure 4:
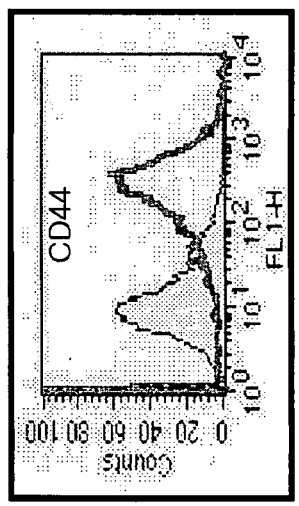
Figure 4:
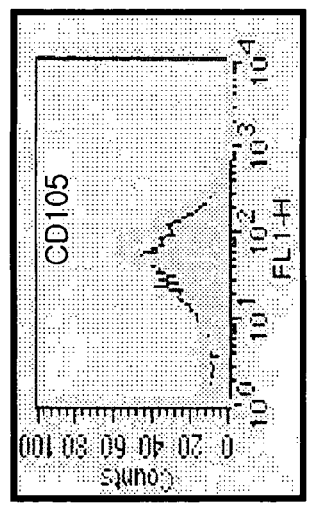

The results showed that overall profiles of surface expression are similar, for example, all the isolated cell lines were strongly positive for CD29, CD44, CD73 (SH3, SH4), CD90, CD105 (SH2), CD166, and HLA-ClassI. However, among the 11 cell surface proteins tested, each stem cell line has relatively unique expression profiles in 9 cell surface protein expressions and similar level of expressions in CD44 and CD90. Further, D5 (#1) cell line was negative for CD31, CD34 and HLA-DR and D5 (#2) was CD31, HLA-DR negative but CD34 was dimly positive, whereas D5 (#3) was positive for CD31, CD34 and HLA-DR (FIG. 4). These results indicate that several different types of stem cells exist in human bone marrow.

Figure 5:
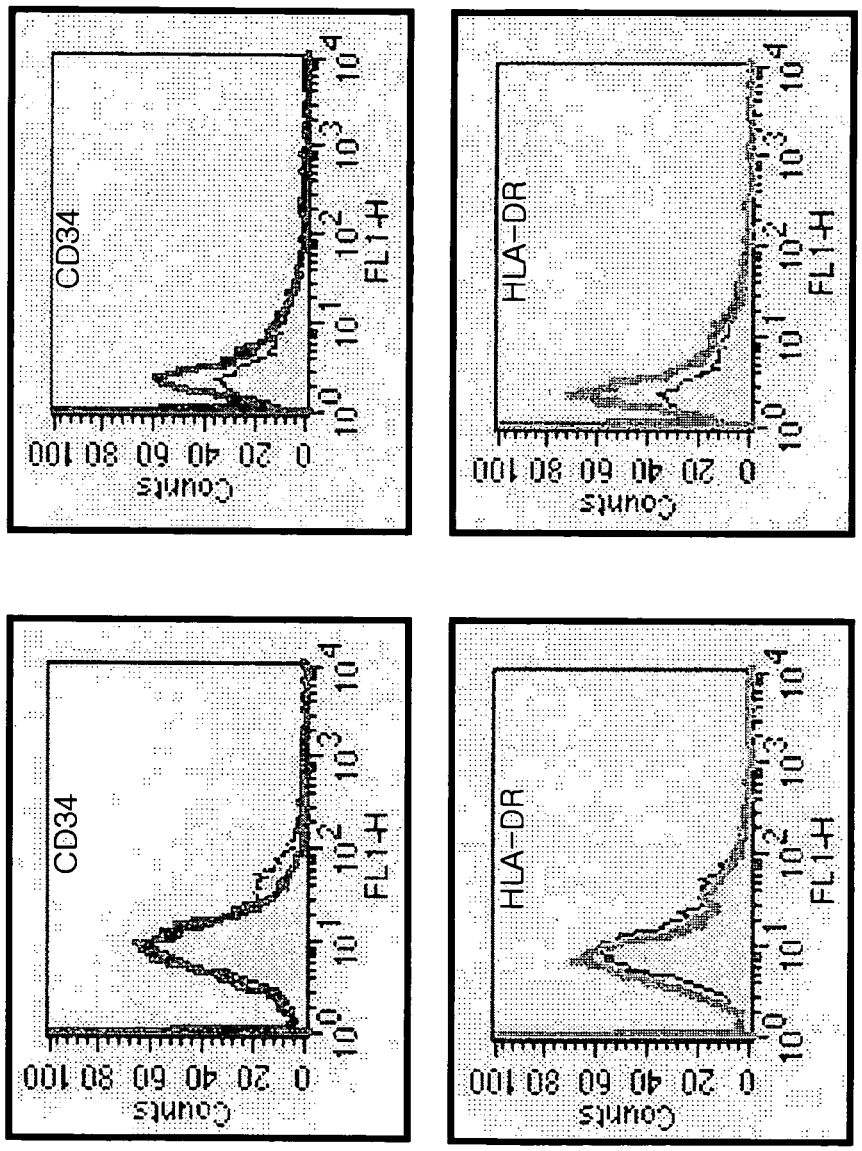
FIG. 5 shows no hematopoietic stem cell surface proteins are observed on isolated MLSCs from bone marrow by a subfractionation culturing method. Flow cytometry analyses showed that MLSCs were negative for HLA-DR and CD34 marker proteins for early hematopoietic stem cells. HMSC8292 (Cambrex Bio Science, Walkersville, Md., USA) cells were used as a control. These results indicate that the isolated MLSCs do not have hematopoietic stem cell phenotypes.

FIG. 5 shows that there are no hematopoietic stem cell surface proteins observed on isolated MLSCs from bone marrow by the inventive subfractionation culturing method. Flow cytometry analyses showed that MLSCs were negative for HLA-DR and CD34 marker proteins for early hematopoietic stem cells. HMSC8292 (Cambrex Bio Science, Walkersville, Md., USA) cells were used as a control. These results indicate that the isolated MLSCs do not have hematopoietic stem cell phenotypes.

Figure 6:
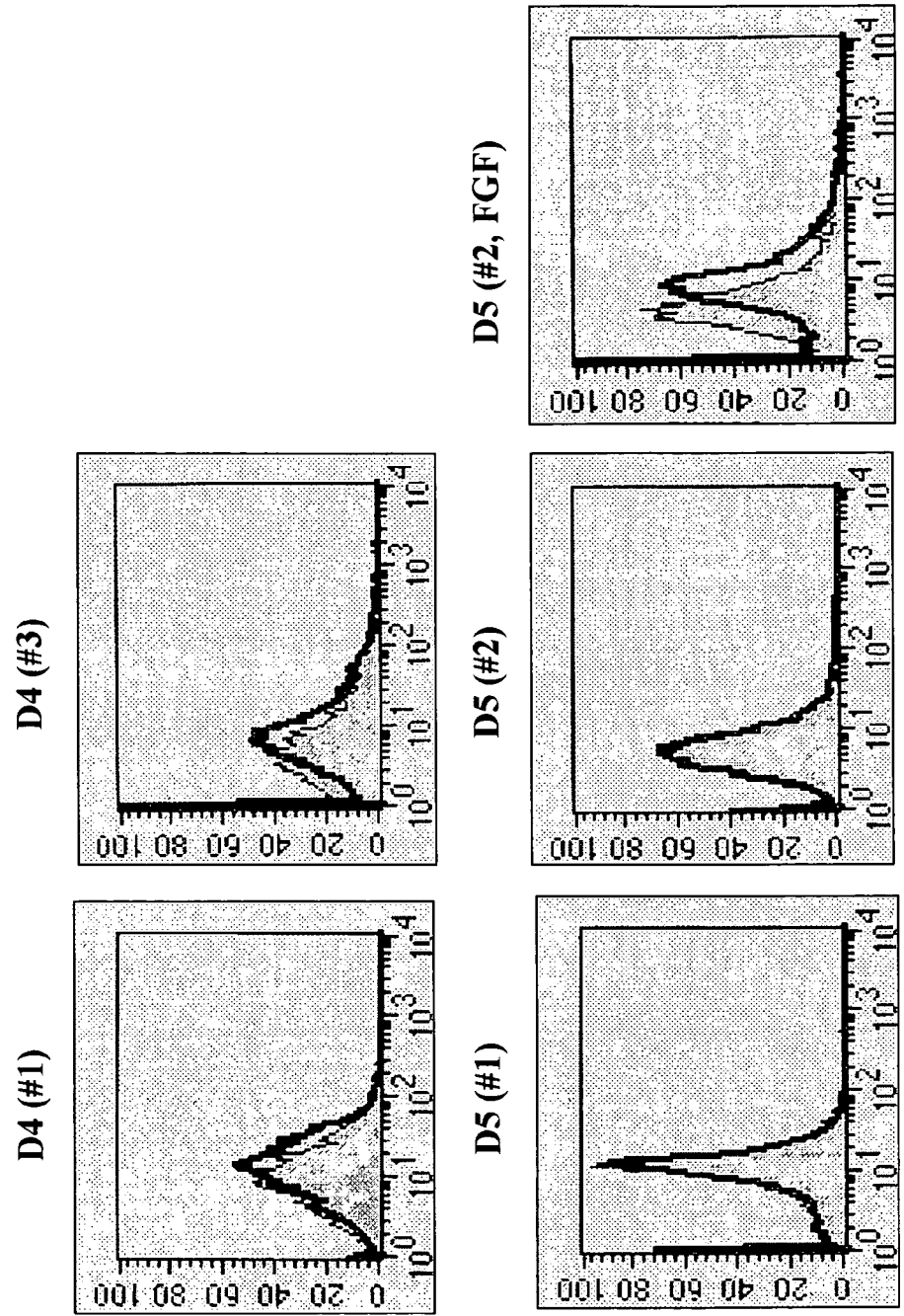
FIG. 6 shows comparison of cell surface protein CD31 (PECAM) expression observed on isolated MLSC lines from bone marrow by a subfractionation culturing method. Expression of CD31 of D4(#1), D4(#3), D5(#1), D5(#2), and D5(#2) with FGF were measured by FACS analysis. The established MLSC line D4(#3) is dimly positive for CD 31, whereas the other MLSC lines are negative. FGF in the growth medium increases the expression of CD31 of D5(#2). These results indicate that D4(#3) has different cell characteristics in differentiation capability and/or cell function.

With respect to the expression of several representative surface proteins markers CD31, CD105, CD73, and CD34 on the isolated cell lineages, FIGS. 6-9 show their comparisons. FIG. 6 shows a comparison of cell surface protein CD31 (PECAM) expression observed on isolated MLSC lines from bone marrow by the inventive subfractionation culturing method. Expression of CD31 of D4(#1), D4(#3), D5(#1), D5(#2), and D5(#2) with FGF were measured by FACS analysis. The established MLSC line D4(#3) is dimly positive for CD 31, whereas the other MLSC lines are negative. FGF in the growth medium increases the expression of CD31 of D5(#2). These results indicate that D4(#3) has different cell characteristics in differentiation capability and/or cell function.

Figure 7:
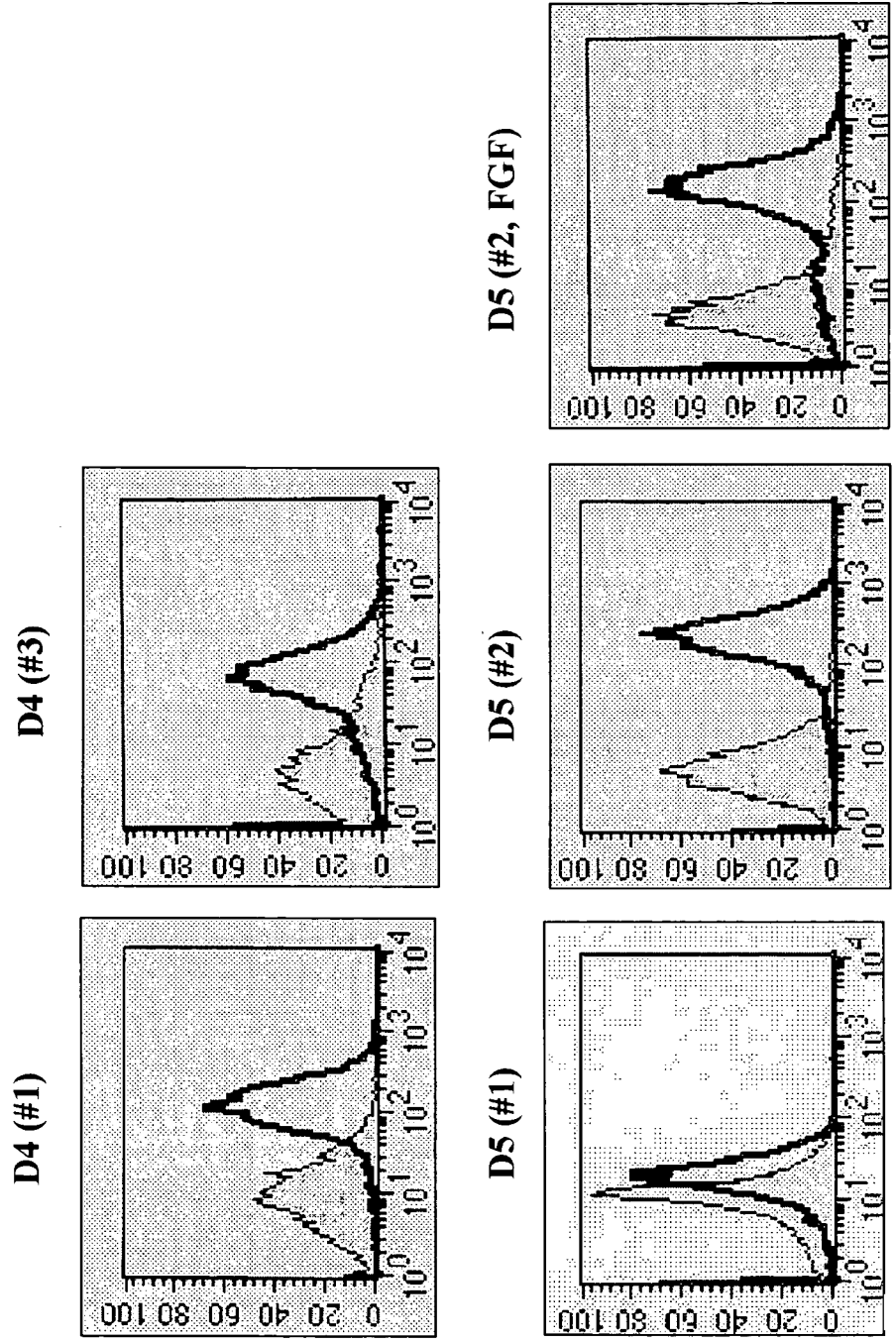
FIG. 7 shows comparison of cell surface protein CD105 (SH2) expression observed on isolated MLSC lines from bone marrow by a subfractionation culturing method. Expression of CD105 of D4(#1), D4(#3), D5(#1), D5(#2), and D5(#2) with FGF were measured by FACS analysis. The established MLSC line D5(#1) shows an intermediate level of CD105 expression, whereas the other stem cell lines show high level of CD105. These results suggest that D5(#1) has different cell characteristics in differentiation capability and/or cell function.

FIG. 7 shows a comparison of cell surface protein CD105 (SH2) expression. The established MLSC line D5(#1) shows an intermediate level of CD105 expression, whereas the other stem cell lines show high level of CD105.

Figure 8:
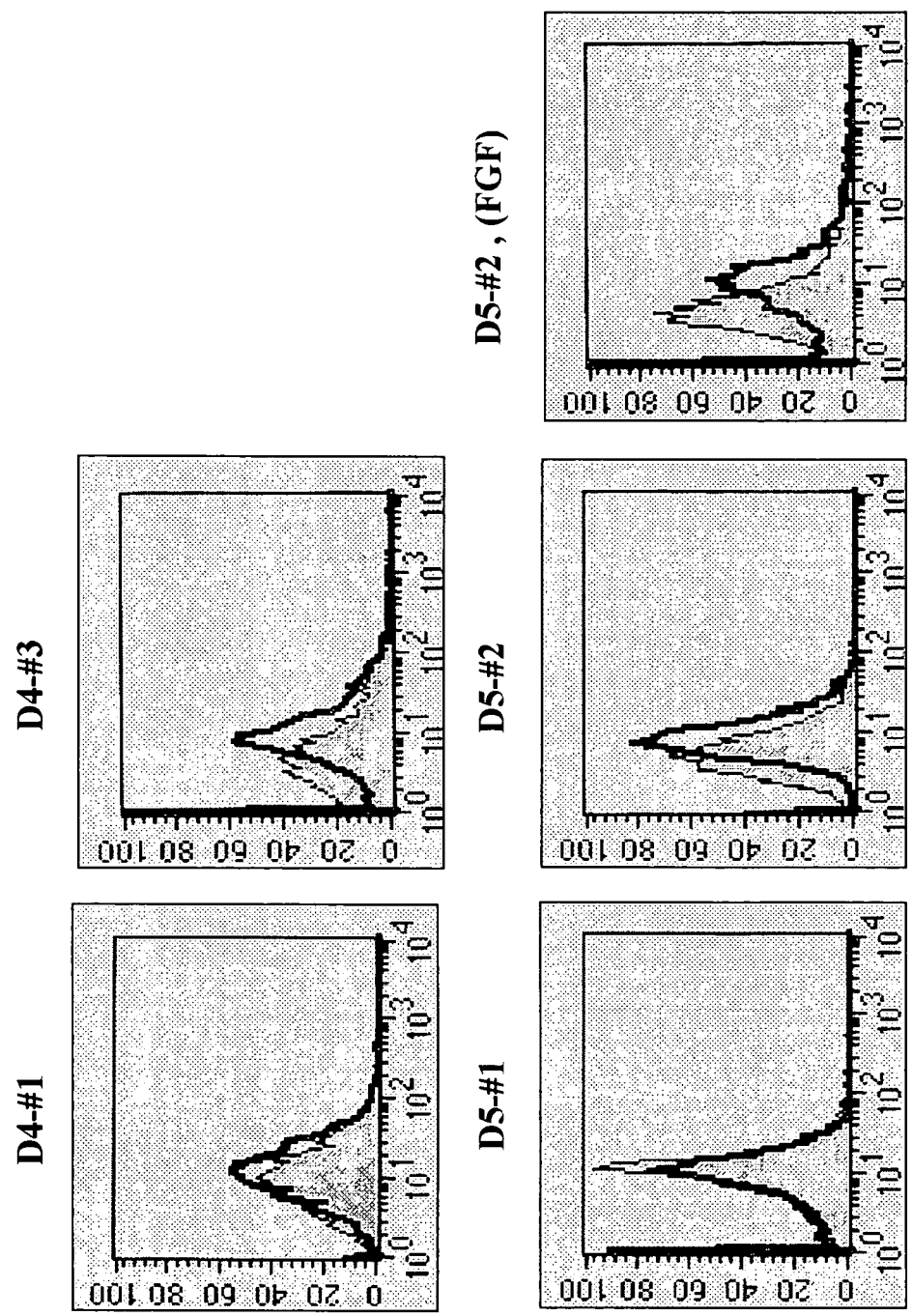
FIG. 8 shows comparison of cell surface protein CD73 (SH3, SH4) expression observed on isolated MLSC lines from bone marrow by a subfractionation culturing method. Expression of CD73 of D4(#1), D4(#3), D5(#1), D5(#2), and D5(#2) with FGF were measured by FACS analysis. The established MLSC line D4(#1) shows a very low level of CD 73 expression and D4(#3) and D5(#2) show an intermediate level, whereas D5(#1) does not express it at all. These results suggest that each stem cell lines has unique cell characteristics in its differentiation capability and/or cell function.

FIG. 8 shows a comparison of cell surface protein CD73 (SH3, SH4) expression. The established MLSC line D4(#1) shows a very low level of CD 73 expression and D4(#3) and D5(#2) show an intermediate level, whereas D5(#1) does not express it at all.

Figure 9:
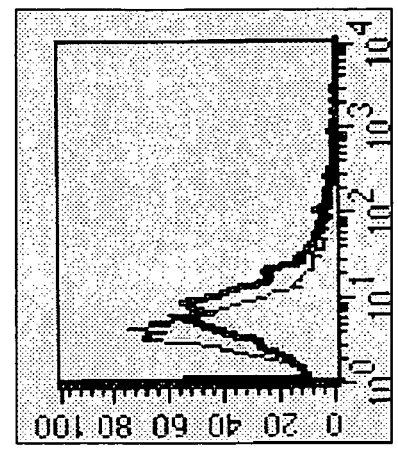
FIG. 9 shows comparison of cell surface protein CD34 expression observed on isolated MLSC lines from bone marrow by a subfractionation culturing method. Expression of CD34 of D4(#1), D4(#3), D5(#1), D5(#2), and D5(#2) with FGF were measured by FACS analysis. The established MLSC lines D4(#3), D4(#3), and D5(#2) show low level of CD34 expression, whereas D5(#1) shows no CD34 expression. These results indicate that each stem cell line has unique cell characteristics in its differentiation capability and/or cell function.
Figure 9:
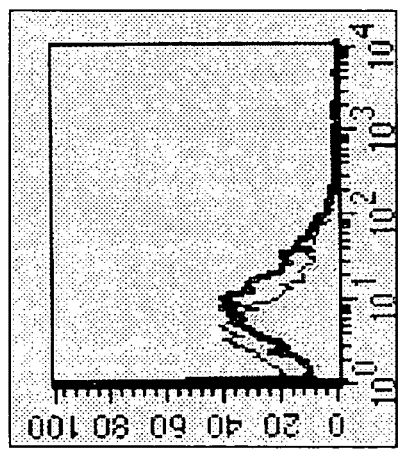
Figure 9:
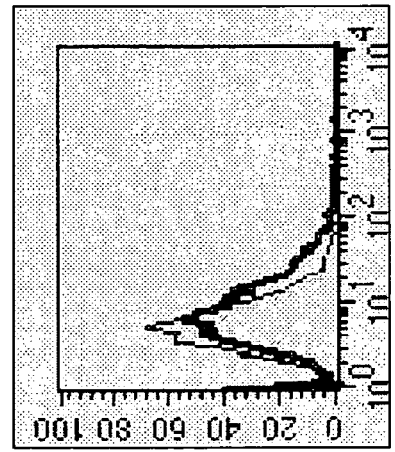
Figure 9:
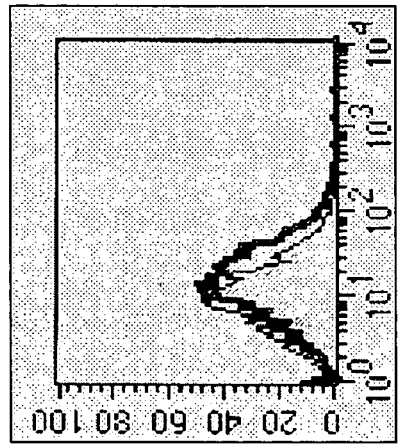
Figure 9:
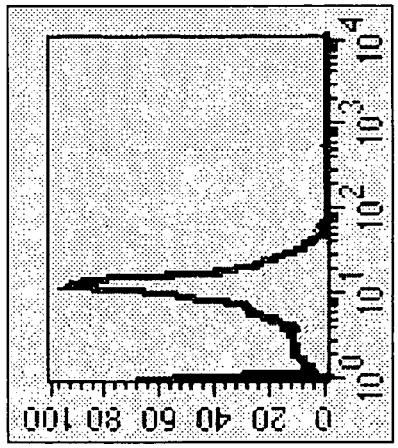

FIG. 9 shows comparison of cell surface protein CD34 expression. The established MLSC lines D4(#3), D4(#3), and D5(#2) show low level of CD34 expression, whereas D5(#1) shows no CD34 expression. The above results indicate that each stem cell line has unique cell characteristics in its differentiation capability and/or cell function.

Example 6.3

Multi-Lineage Differentiation of Bone Marrow Cell Lines

In order to determine the differentiation capacity of the single-cell derived bone marrow cell lines, chondrogenic, osteogenic, and adipogenic differentiation were tested by pellet-culture system and neurogenic and hepatogenic differentiation by normal cell culture in each cell-specific induction medium. All the isolated cell lines were capable of differentiating into chondrogenic, osteogenic, adipogenic, neurogenic and hepatogenic lineages (Table 2). The four isolated MLSC lines showed different level of differentiation capability. For example, D5(#2) stem cell line is capable of differentiating to chondrocyte, osteocyte, adipocyte, hepatocyte, and neural cells, whereas others have different level of differentiation capability in osteogenic, neurogenic, or hepatogenic lineage.

TABLE 2

Summary of differentiation capability of the isolated MLSC lines

| | D4 (#1) | D4 (#3) | D5 (#1) | D5 (#2) | D5(#2, FGF) |
|---|---|---|---|---|---|
| Chondrogenic | H | H | H | H | I |
| Osteogenic | N | L | I | H | H |
| Adipogenic | H | H | H | H | H |
| Neurogenic | I | H | L | H | H |
| Hepatogenic | L | L | N | H | H |

(N—negative, L—low, I—intermediate, H—high)

Example 6.4

Chondrogenic Differentiation of Bone Marrow Cell Lines

Figure 10:
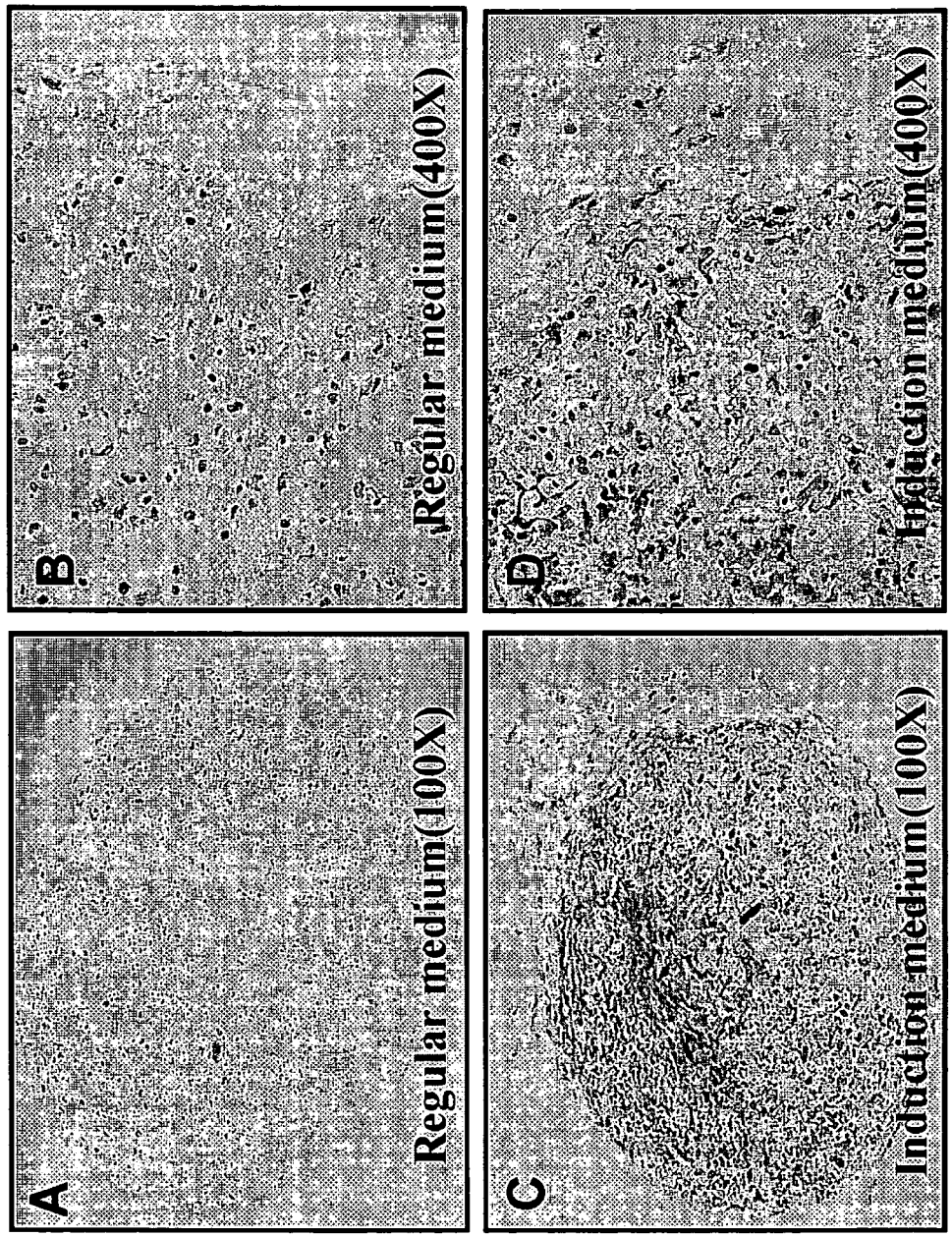
FIGS. 10A-10D show chondrogenic differentiation of the isolated MLSCs. Histochemical stain with Toluidine-blue showed that chondrogenically differentiated MLSCs were highly positive for the stain, tested 21 days after chondrogenic induction. (A & B) Cell pellet grown in regular medium. (C & D) Cell pellet grown in chondrogenic induction medium. The results show that MLSCs grown in chodrogenic induction medium secrete high level of proteoglycans and can be differentiated into chodrocytes.

Four single-cell derived bone marrow cell lines at passage 3 or 4 were pellet-cultured in chondrogenic differentiation medium (6.25 µg/ml insulin, transferrin, 6.25 ng/ml selenous acid, 1.25 mg/ml BSA, 5.35 µg/ml linoleic acid, TGF-β1 10 ng/ml, and TGF-β3 10 ng/ml). Chondrogenic differentiation was achieved 14 to 21 days following treatment. Positive toludine blue histochemical stain and type II collagen-rich extracellular matrix by immunohistochemical stain was evident (FIG. 10). In contrast, the cell lines cultured in normal culture medium showed negative stain.

Example 6.5

Osteogenic Differentiation of Bone Marrow Cell Lines

Figure 11:
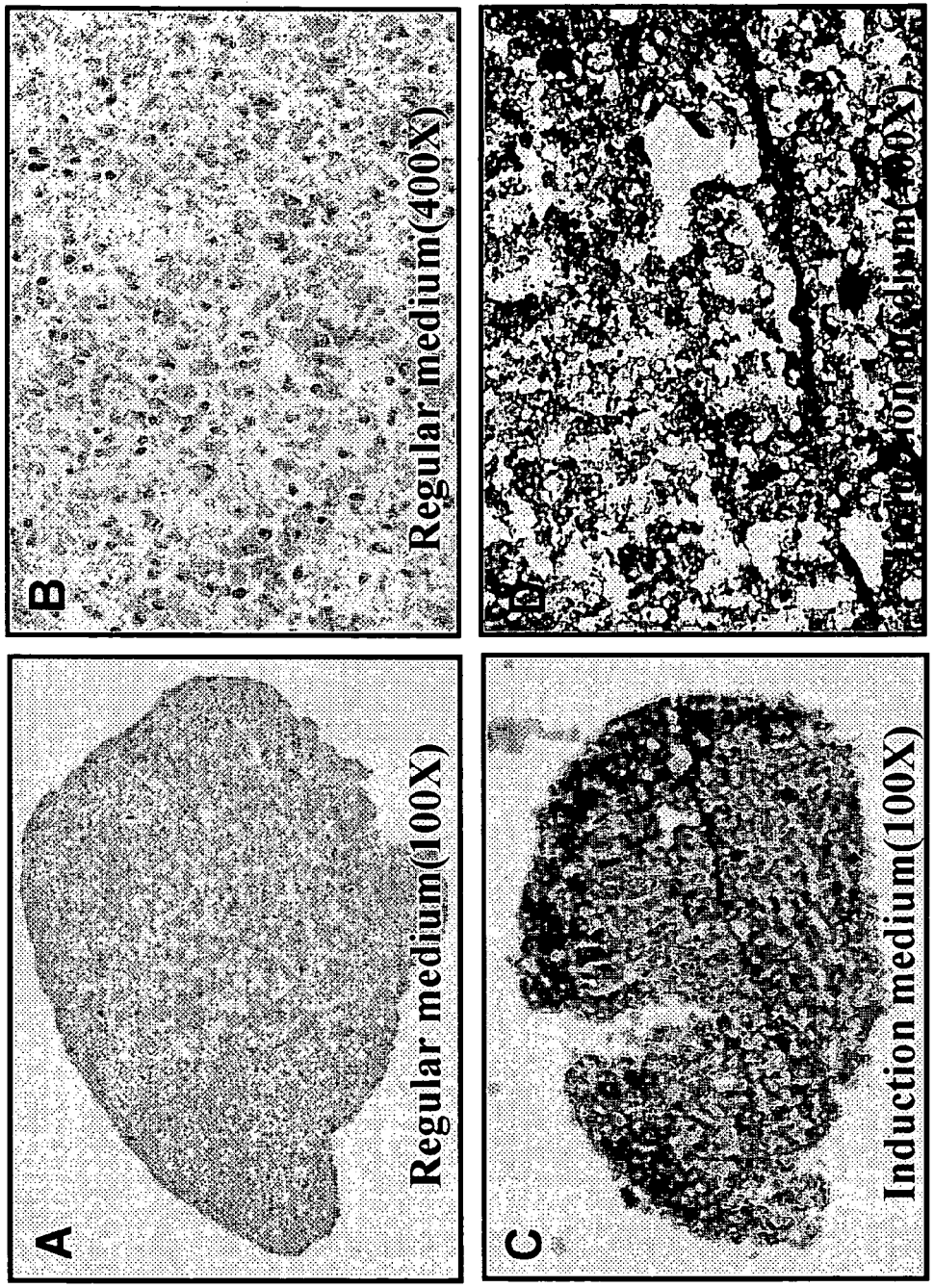
FIGS. 11A-11D show. Osteogenic differentiation of the isolated MLSCs. Histochemical stain with von Kossa stain showed the presence of mineral associated with the matrix in the osteogenically differentiated MLSCs, 21 days after osteogenic induction. (A & B) Cell pellet grown in regular medium. (C & D) Cell pellet grown osteogenic induction medium. The results show that MLSCs grown in osteogenic induction medium can make high level of calcium and can be differentiated into osteocytes.

Four single-cell derived bone marrow cell lines at passage 3 or 4 were pellet-cultured in osteogenic differentiation medium (50 µg/ml ascorbate 2-phosphate, $10^{-8}$ M dexamethasone, and 10 mM β-glycerophosphate). Osteogenic differentiation was achieved 14 to 21 days following the treatment. Postitive von Kossa staining was evident in the cells grown in osteogenic differentiation medium, while the control cells grown in normal culture was not (FIG. 11).

Example 6.6

Adipogenic Differentiation of Bone Marrow Cell Lines

Figure 12:
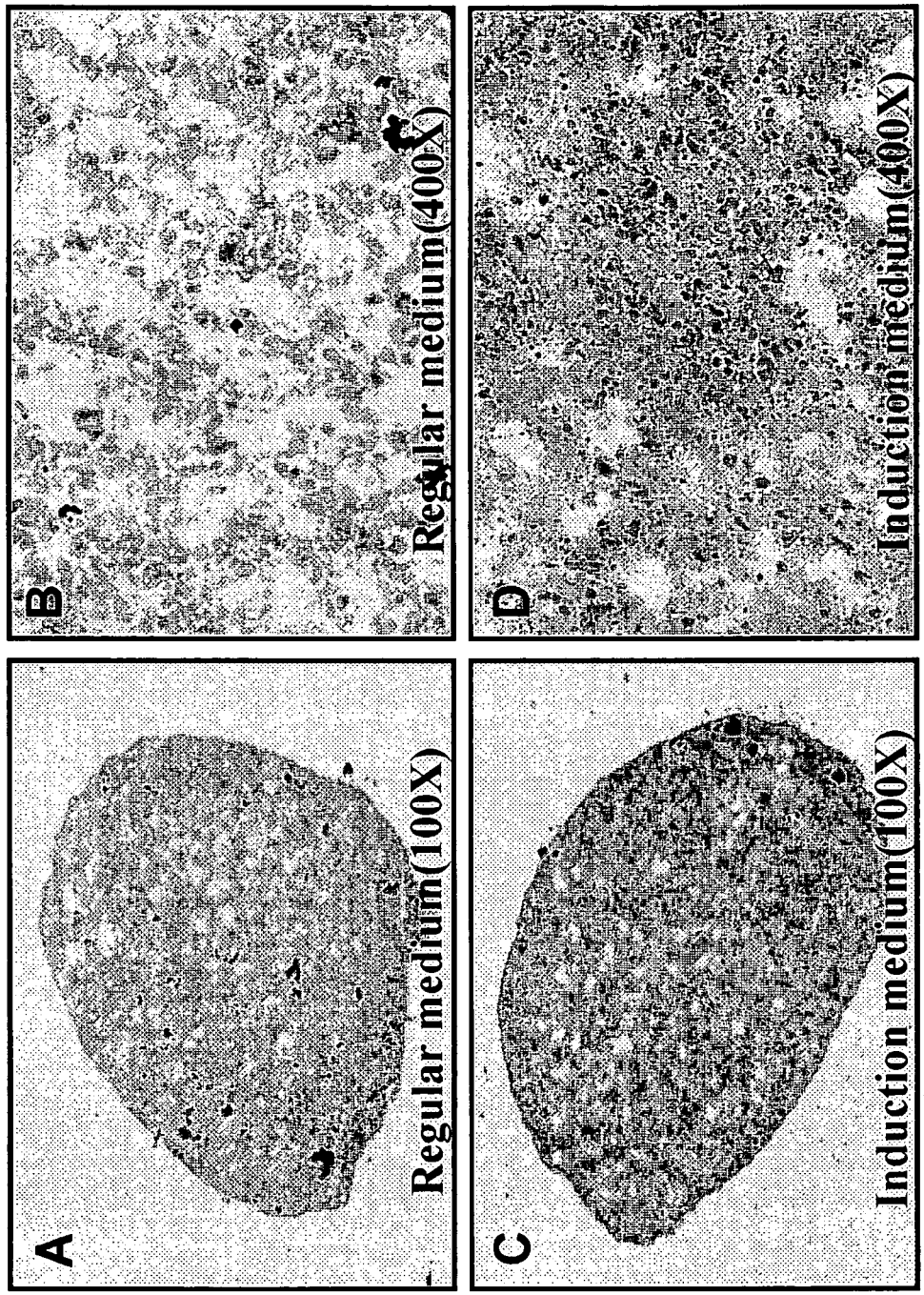
FIGS. 12A-12D. Adipogenic differentiation of the isolated MLSCs. Histochemical stain with Oil red-O showed that adipogenically differentiated MLSCs were highly positive for the stain, tested 21 days after adipogenic induction. (A & B) Cell pellet grown in regular medium. (C & D) Cell pellet grown adipogenic induction medium. The results show that MLSCs grown in adipogenic induction medium can produce neutral lipid vacuoles and can be differentiated into adipocytes.

Four single-cell derived bone marrow cell lines at passage 3 or 4 were pellet-cultured in adipogenic differentiation medium (50 µg/ml ascorbate 2-phosphate, $10^{-7}$ M dexamethasone, and 50 µg/ml indomethacine). Adipogenic differentiation was achieved 14 to 21 days following treatment. Positive Oil red-O staining was evident in the adipogenic differentiated cells, whereas no stain was detected in the control cells grown in normal culture medium (FIG. 12).

Example 6.7

Neurogenic Differentiation of Bone Marrow Cell Lines

Figure 13:
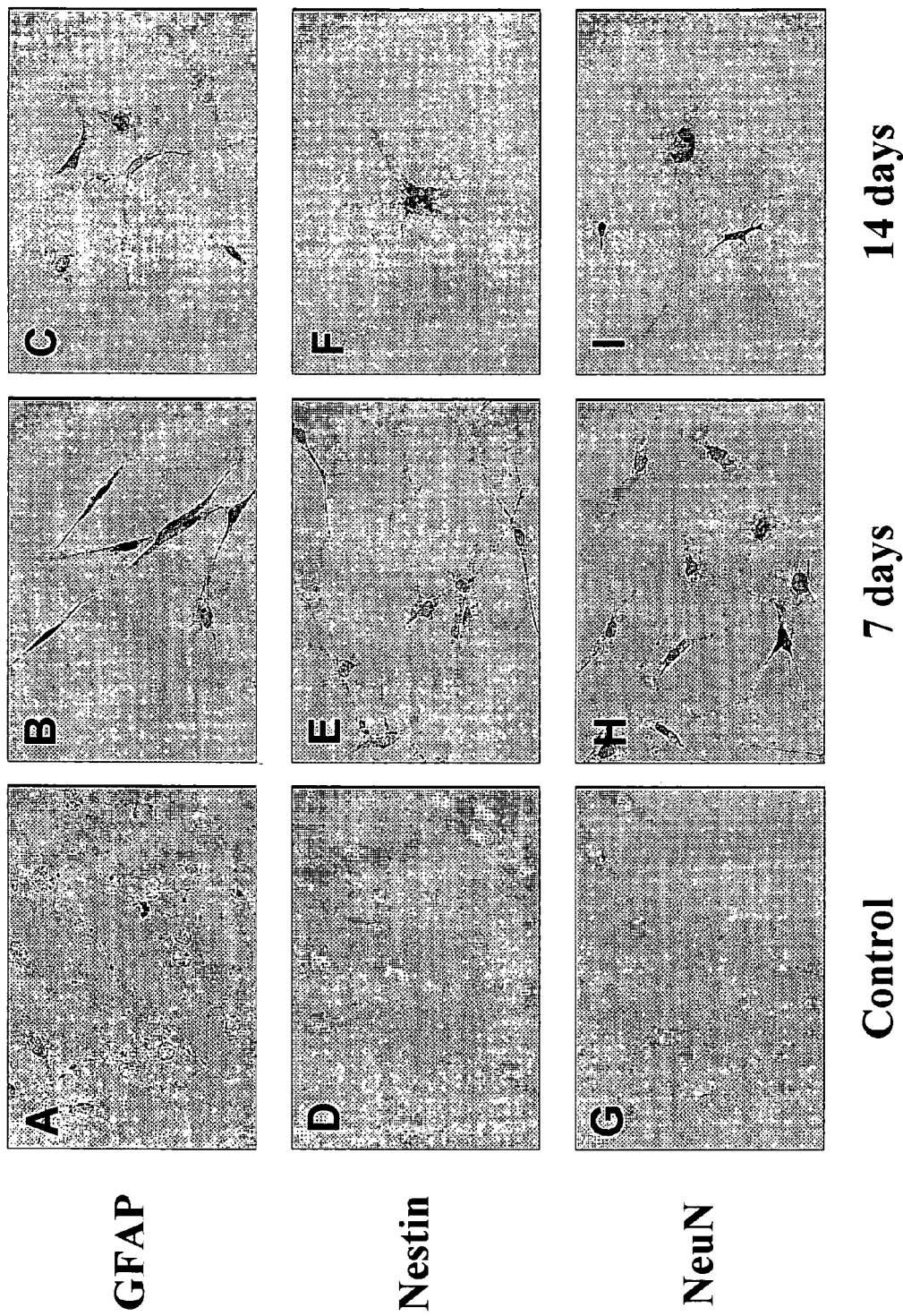
FIGS. 13A-13I show neurogenic differentiation of the isolated MLSCs. Immunohistological stain with GFAP, Nestin, and NeuN antibodies showed that neurogenically differentiated MLSCs were highly positive for the stain, tested 7 and 14 days after neurogenic induction. (A, D & G) MLSCs grown in normal culture medium and incubated with the antibodies. (B, E & H) Cells stained with each antibody 7 days after neurogenic induction. (C, F & I) Cells stained with each antibody 14 days after neurogenic induction. The results show that MLSCs grown in neurogenic induction medium can synthesize glial cell specific protein, glial fibrillary acidic protein (GFAP), early and late neural cell marker proteins, Nestin and NeuN, respectively and can be differentiated into neural cells.

Four single-cell derived bone marrow cell lines at passage 3 or 4 were cultured in neurogenic differentiation medium (1 mM dibutyryl cyclin AMP, 0.5 mM isobutyl methylxanthine, 20 ng/ml human epidermal growth factor, 40 ng/ml basic fibroblast growth factor-8, 10 ng/ml fibroblast growth factor-8, 10 ng/ml, brain-derived neurotrophic factor). Neurogenic differentiation was achieved 14 to 21 days following treatment. Positive GAFP, NueN, and Nestin staining was evident in the neurogenic differentiated cells, whereas no stain was detected in the control cells grown in normal culture medium (FIG. 13).

Figure 14:
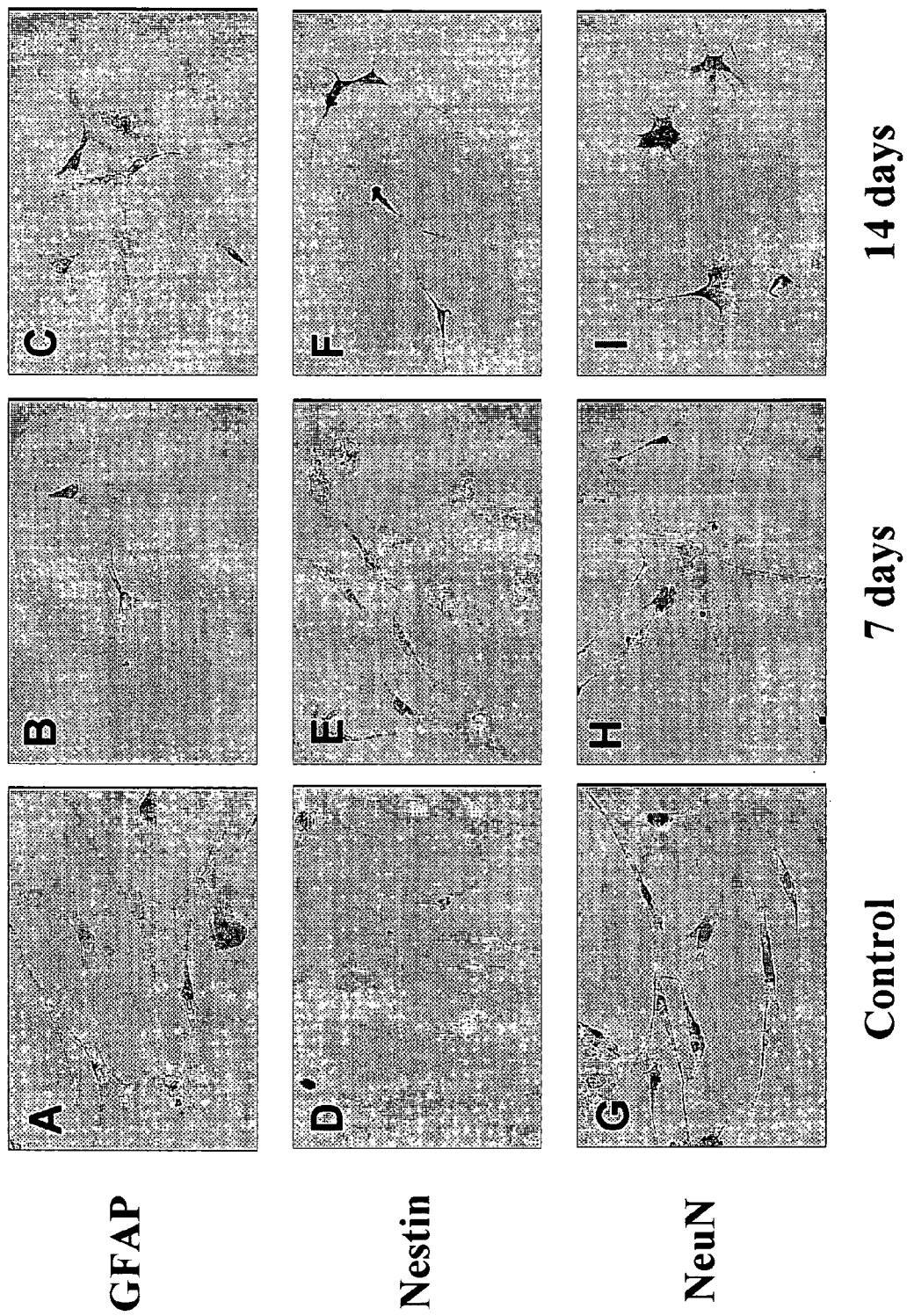
FIGS. 14A-14I show neurogenic differentiation of the isolated MLSCs grown with FGF. Immunohistological stain with GFAP, Nestin, and NeuN antibodies showed that neurogenically differentiated MLSCs grown with FGF were highly positive for the stain, tested 7 and 14 days after neurogenic induction. (A, D & G) MLSCs grown in normal culture medium and incubated with the antibodies. (B, E & H) Cells stained with each antibody 7 days after neurogenic induction. (C, F & I) Cells stained with each antibody 14 days after neurogenic induction. The results show that MLSCs grown in neurogenic induction medium with FGF can also synthesize glial cell specific protein (GFAP), early and late neural cell marker proteins, Nestin and NeuN, respectively and can be differentiated into neural cells.

Furthermore, FIG. 14 shows neurogenic differentiation of the isolated MLSCs grown with FGF. Immunohistological stain with GFAP, Nestin, and NeuN antibodies showed that neurogenically differentiated MLSCs grown with FGF were highly positive for the stain, tested 7 and 14 days after neurogenic induction. MLSCs grown in neurogenic induction medium with FGF can also synthesize glial cell specific protein (GFAP), early and late neural cell marker proteins, Nestin and NeuN, respectively and can be differentiated into neural cells. This signifies that culturing the isolated cells with FGF did not change the neurogenic differentiation capability.

Example 6.8

Hepatogenic Differentiation of Bone Marrow Cell Lines

Figure 15:
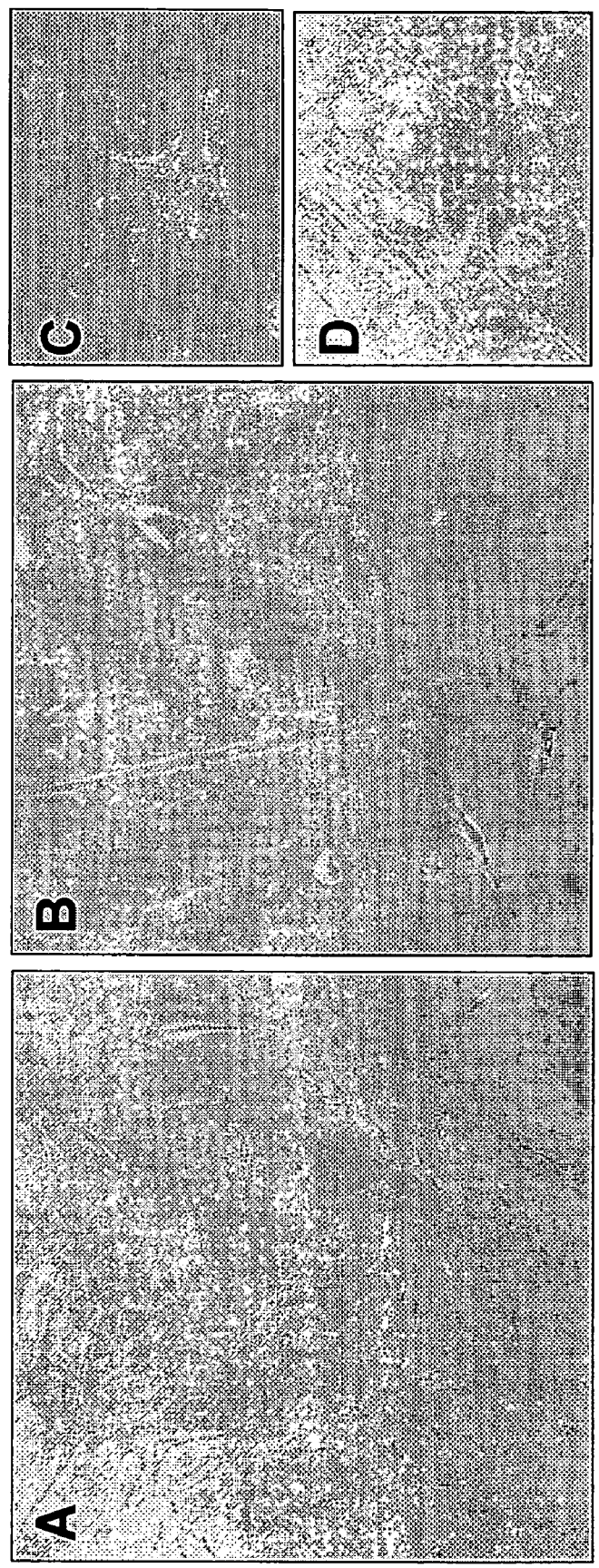
FIGS. 15A-15D shows morphological changes of the isolated MLSCs grown in hepatogenic induction medium. Morphological changes were observed 14 days after growing in hepatogenic induction medium. (A) Morphology of MLSCs grown in normal culture medium. (B, C & D) Hepatological morphology changes of MLSCs grown in hepatogenic induction medium for 14 days. The results show that MLSCs grown in hepatogenic induction medium can be differentiated into hepatocytes.

Four single-cell derived bone marrow cell lines at passage 3 or 4 were cultured in hepatogenic differentiation medium differentiation medium containing 20 mg/ml hepatocyte growth factor (R&D), 10 ng/ml oncostatin-M (R&D), 10 ng/ml epidermal growth factor (sigma), 20 ng/ml fibroblast growth factor-4 (R&D), 10 ng/ml basic-fibroblast growth factor (sigma), 50 mg/ml ITS+premix (Becton Dickinson; 6.25 ug/ml insulin, 6.25 ug/ml transferrin, 6.25 ng/ml selenius acid, 1.25 mg/ml BSA, 5.35 mg/ml linoleic acid)), 0.1 µM ascorbate 2-phosphate (sigma), $10^{-8}$ M dexamethasone (sigma). Medium was changed every 3 days (FIG. 15).

Example 6.9

Figure 16:
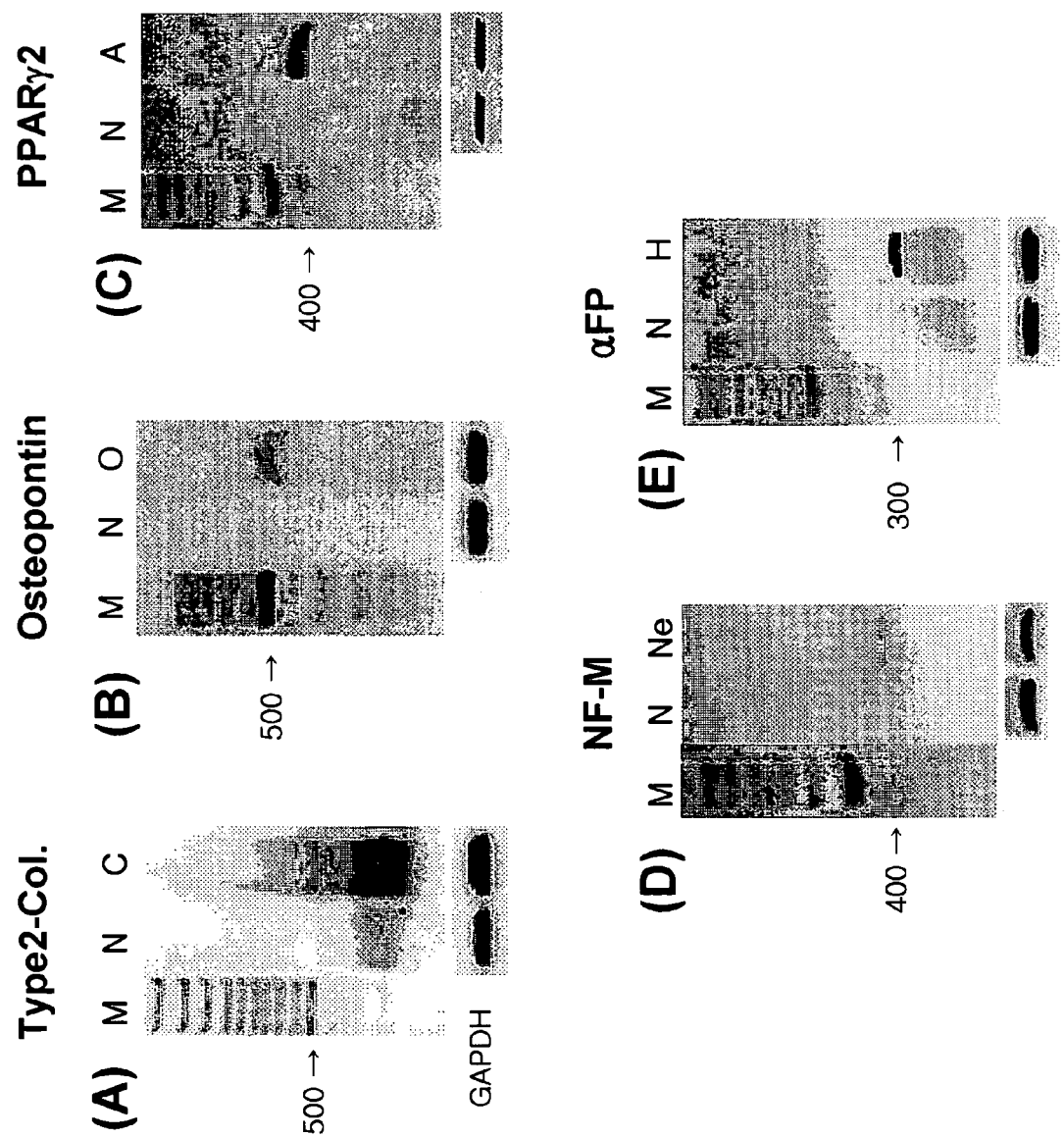
FIGS. 16A-16E show observation of chondrocyte, osteocyte, adipocyte, hepatocyte, and neural cell specific gene expression by RT-PCR analysis. Total RNA was analyzed by RT-PCR for the expression of (A) type II collagen (chondrogenic, 500 bp), (B) osteopontin (osteogenic, 330 bp), (C) peroxisome proliferator activated receptor gamma 2 (PPARγ2) (adipogenic, 352 bp), (D) neurofilament molecule (NF-M) (neurogenic, 430 bp), and (E) alpha feto protein (αFP) (hepatogenic, 216 bp). Expression of Glyceraldehyde-3-phosphate dehydrogenase (GAPDH) was used as an internal control. M; DNA molecular size markers, N: non-induced, C: chondrogenic, O: osteogenic, A: adipogenic, Ne: neurogenic, and H: hepatogenic. These results strongly indicate that the isolated MLSCs can express cell-specific genes in each specific differentiation condition and can be differentiated into multi-lineages.

Cartilage, Bone, Fat, Neuron, and Hepatocyte-Specific Gene Expression of Bone Marrow Cell Lines In order to measure the expression of cartilage, bone, fat, neuron and hepatocyte specific genes in the differentiated single-cell derived bone marrow cell lines, RT-PCR analysis was performed with passage 4 or 5 cells. Lineage specific gene expression of cartilage (type II collagen), bone (osteopontin), fat (PPARγ2), neuron (NF-M), and hepatocyte (αFP) were detected in the differentiated cells (FIG. 16). In contrast, these genes were not expressed in non-differentiated control cells. Expression of GAPDH was used as an internal control. These results strongly indicate that the isolated MLSCs can express cell-specific genes in each specific differentiation condition and can be differentiated into multilineages.

Example 6.10

Expression of Cytokines of Bone Marrow Cell Lines

Figure 17:
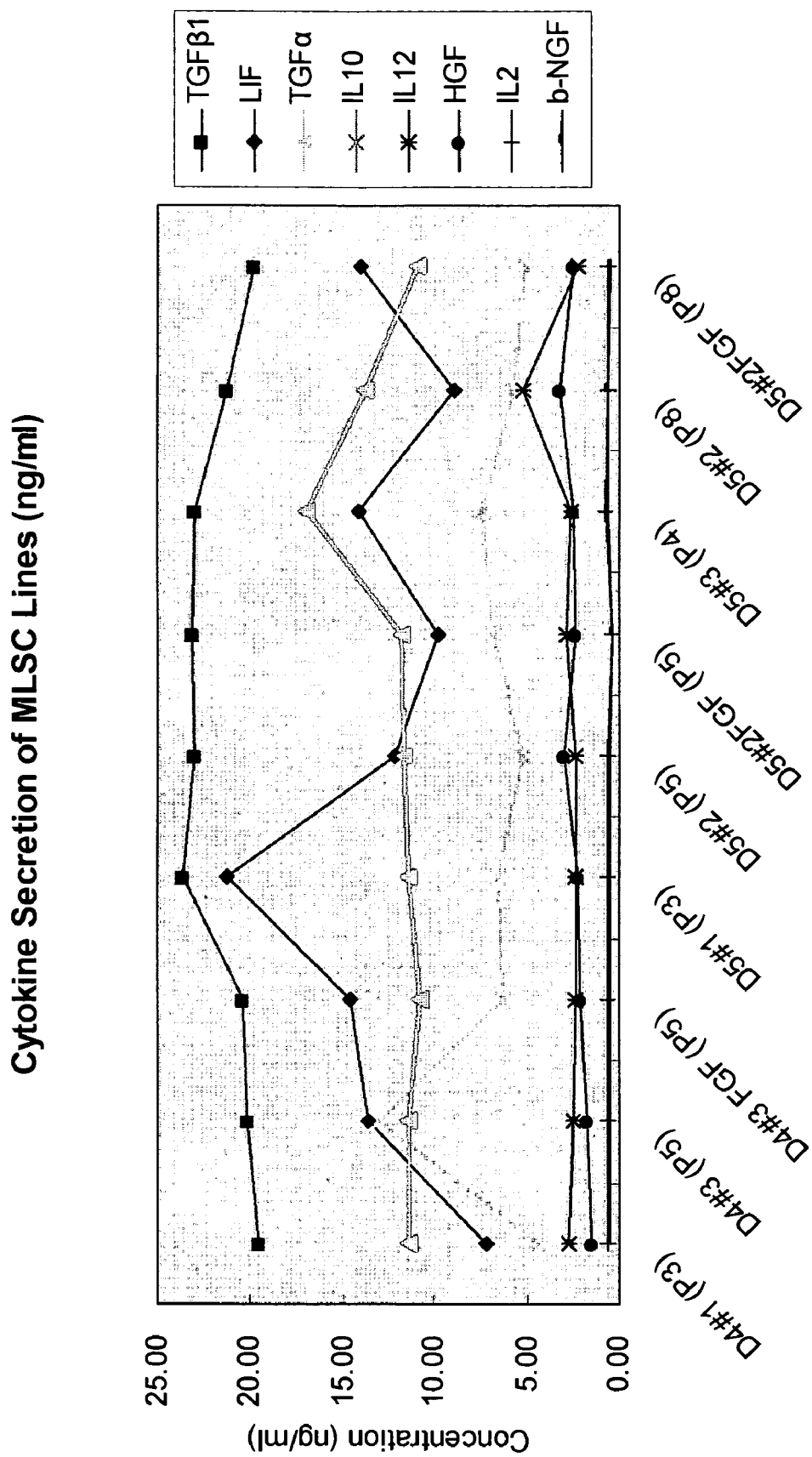
FIG. 17 shows cytokine secretion of isolated MLSC lines. Aliquots (50~100 μl) of the MLSC culture supernatant were analyzed by ELISA using the Quantikine® Human TGF-β1, b-NGF, LIF, IL10, HGF, IL2, TGF-α and IL12. TGF-β1, LIF, TGF-α, and IL10 showed high levels of secretion, whereas the others showed low or no secretion. High level of TGF-β1 secretion by the isolated MLSCs indicates that these stem cells can play a role in suppression of T-cell activation. Also, relatively high level of other cytokines, such as LIF, TGF-α, and IL10, suggest that these cells may have immune-modulation activities.

FIG. 17 shows cytokine secretion of isolated MLSC lines. Aliquots (50~100 µl) of the MLSC culture supernatant were analyzed by ELISA using the Quantikine® Human TGF-β1, b-NGF, LIF, IL10, HGF, IL2, TGF-α and IL12. TGF-β1, LIF, TGF-α, and IL10 showed high levels of secretion, whereas the others showed low or no secretion. High level of TGF-β1 secretion by the isolated MLSCs indicates that these stem cells can play a role in suppression of T-cell activation. Also, relatively high level of other cytokines, such as LIF, TGF-α, and IL10, suggest that these cells may have immune-modulation activities.

All of the references cited herein are incorporated by reference in their entirety.

REFERENCES

1. Shizuru J A, Negrin R S, Weissman I L. Hematopoietic stem and progenitor cells: Clinical and Preclinical Regeneration of the Hematolymphoid System. Annu Rev Med 2005; 56:509-538.

2. Barry F P, Murphy J M. Mesenchymal stem cells: clinical applications and biological characterization. Int J Biochem Cell Biol 2004; 36:568-584.

3. Pittenger M F, Mackay A M, Beck S C, Jaiswal R K, Douglas R, Mosca J D, Moorman M A, Simonetti D W, Craig S, Marshak D R. Multilineage potential of adult human mesenchymal stem cells. Science 1999; 284:143-147.

4. Friedenstein A J P, Petrokova K V. Osteogenesis in transplants of bone marrow cells. Journal of Embyological Experimental Morphology 1966; 16:381-390.

5. Friedenstein A J, Gorskaja J F, Kulagina N N. Fibroblast precursors in normal and irradiated mouse hematopoietic organs. Exp Hematol 1976; 4:267-274.

6. Jiang Y, Jahagirdar B N, Reinhardt R L, Schwartz R E, et al. Pluripotency of mesenchymal stem cells derived from adult marrow. Nature 2002; 418:41-49.

7. Reyes M, Verfaillie C M. Characterization of multipotent adult progenitor cells, a subpopulation of mesenchymal stem cells. Ann N Y Acad Sci 2001; 938:231-233.

8. Jorgensen C, Gordeladze J, Noel D. Tissue engineering through autologous mesenchymal stem cells. Curr Opin Biotechnol 2004; 15:406-410.

9. Engineering mesenchymal stem cells for immunotherapy. Gene Ther 2003; 10:928-931.

10. Le Blanc K, Tammik C, Rosendahl K, Zetterberg E, Ringden O. HLA expression and immunologic properties of differentiated and undifferentiated mesenchymal stem cells. Exp Hematol 2003; 31:890-896.

11. Kassem M, Kristiansen M, Abdallah B M. Mesenchymal stem cells: cell biology and potential use in therapy. Basic & Clinical Pharmacology & Toxicology 2004; 95:209-214.

12. Rickard D J, Kassem M, Hefferan T E et al. Isolation and characterization of osteoblast precursor cells from human bone marrow. J Bone Miner Res 1996; 11:312-324.

13. Zohar R, Sodek J, McCulloch C A. Characterization of stromal progenitor cells enriched by flow cytometry. Blood 1997; 90:3471-3481.

14. van Vlasselaer P, Falla N, Snoeck H et al. Characterization and purification of osteogenic cells from murine bone marrow by two-color cell sorting using anti-Sca-1 monoclonal antibody and wheat germ agglutinin. Blood 1994; 84:753-763.

Simmons P J, Torok-Storb B. Identification of stromal cell precursors in human bone marrow by a novel monoclonal antibody, STRO-1. Blood 1991; 78:55-62.

Long M W, Robinson J A, Ashcraft E A et al. Regulation of human bone marrow-derived osteoprogenitor cells by osteogenic growth factors. J Clin Invest 1995; 95:881-887.

Waller E K, Olweus J, Lund-Johansen F et al. The "common stem cell" hypothesis reevaluated: human fetal bone marrow contains separate populations of hematopoietic and stromal progenitors. Blood 1995; 85:2422-2435.

Joyner C J, Bennett A, Triffitt J T. Identification and enrichment of human osteoprogenitor cells by using differentiation stage-specific mAbs. Bone 1997; 21:1-6.

19. Reyes M, Lund T, Lenvik T et al. Purification and ex vivo expansion of postnatal human marrow mesodermal progenitor cells. Blood 2001; 98:2615-2625.

20. Clark B R, Keating A. Biology of bone marrow stroma. Ann NY Acad Sci 1995; 770:70-78.

21. Phinney D G, Kopen G, Isaacson R L et al. Plastic adherent stromal cells from the bone marrow of commonly used strains of inbred mice: variations in yield, growth, and differentiation. J Cell Biochem 1999; 72:570-585.

22. Colter D C, Class R, DiGirolamo C M et al. Rapid expansion of recycling stem cells in cultures of plastic-adherent cells from human bone marrow. Proc Natl Acad Sci USA 2000; 97:3213-3218.

23. Prockop D J, Sekiya I, and Colter D C. Isolation and characterization of rapidly self-renewing stem cells from cultures of human marrow stromal cells. Cytotherapy 2001; 3(5):393-396.

24. Hung S C, Chen N J, Hsieh S L et al. Isolation and characterization of size-sieved stem cells from human bone marrow. Stem Cells 2002; 20:249-258.

25. Schwarz E J, Alexander G M, Prockop D J et al. Multipotential marrow stromal cells transduced to produce L-DOPA: engraftment in a rat model of Parkinson disease. Hum Gene Ther 1999; 10:2539-2549.

26. Schwarz E J, Reger R L, Alexander G M et al. Rat marrow stromal cells rapidly transduced with a self-inactivating retrovirus synthesize L-DOPA in vitro. Gene Ther 2001; 8:1214-1223.

27. Koc O N, Gerson S L, Cooper B W et al. Rapid hematopoietic recovery after coinfusion of autologous-blood stem cells and culture-expanded marrow mesenchymal stem cells in advanced breast cancer patients receiving high-dose chemotherapy. J Clin Oncol 2000; 18:307-316.

28. Horwitz E M, Prockop D J, Fitzpatrick L A et al. Transplantability and therapeutic effects of bone marrow-derived mesenchymal cells in children with osteogenesis imperfecta. Nat Med 1999; 5:309-313.

29. Horwitz E M, Prockop D J, Gordon P L et al. Clinical responses to bone marrow transplantation in children with severe osteogenesis imperfecta. Blood 2001; 97:1227-1231.

Those skilled in the art will recognize, or be able to ascertain using no more than routine experimentation, many equivalents to the specific embodiments of the invention specifically described herein. Such equivalents are intended to be encompassed in the scope of the claims.

What is claimed is:

1. A method of obtaining a homogeneous population of single cell-derived clonal multipotent bone marrow cells based on cell density from a biological sample of bone marrow, comprising:
 (i) allowing the biological sample to settle by gravity in a first container producing a first supernatant of lower density cells;
 (ii) transferring the first supernatant directly without undergoing centrifugation to a second container of growth medium and allowing cells to settle to the bottom producing a second supernatant of lower density cells;
 (iii) transferring the second supernatant directly without undergoing centrifugation to a third container of growth medium and allowing cells to settle to the bottom, producing a third supernatant of lower density cells;
 (iv) transferring the third supernatant directly without undergoing centrifugation to another container of growth medium and allowing cells to settle to the bottom, producing another supernatant of lower density cells;
 (v) allowing single-cell derived colonies to appear on the bottom of the container of step (iv);
 (vi) isolating the single-cell derived colonies; and
 (vii) expanding cells from the single-cell derived colonies in a further other container of growth medium to obtain the homogeneous population of single cell-derived clonal multipotent bone marrow cells.

2. The method according to claim 1, wherein the cells are settled for one day in step (iv).

3. The method according to claim 1, wherein the isolated cells from the supernatant are expanded in a container.

4. The method according to claim 1, wherein the container has a flat bottom.

5. The method according to claim 1, wherein the container is coated with a cell adhesive agent.

6. The method according to claim 5, wherein the cell adhesive agent comprises a polymer of any charged amino acids.

7. The method according to claim 6, wherein the cell adhesive agent is collagen, polylysine, polyarginine, polyaspartate, polyglutamate, or a combination thereof.

8. The method according to claim 1, comprising contacting the isolated cells with a connective tissue cell transforming/differentiating medium, thereby forming mesoderm lineage cells.

9. The method according to claim 8, wherein the mesoderm lineage cells are connective tissue cells.

10. The method according to claim 9, wherein the connective tissue cells are chondrocytes, and the transforming/differentiating medium is chondrocyte transforming/differentiating medium.

11. The method according to claim 9, wherein the connective tissue cells are adipocytes, and the transforming/differentiating medium is adipocyte transforming/differentiating medium.

12. The method according to claim 9, wherein the connective tissue cells are osteocytes, and the transforming/differentiating medium is osteocyte transforming/differentiating medium.

13. The method according to claim 1, comprising contacting the isolated cells in with an ectoderm tissue cell transforming/differentiating medium thereby forming ectoderm lineage cells.

14. The method according to claim 13, wherein the ectoderm lineage cells are neural tissue cells, and the transforming/differentiating medium is neural tissue transforming/differentiating medium.

15. The method according to claim 1, comprising contacting the isolated cells with an endoderm tissue cell transforming/differentiating medium thereby forming endoderm lineage cells.

16. The method according to claim 15, wherein the endoderm lineage cells are hepatogenic tissue cells, and the transforming/differentiating medium is hepatogenic tissue cell transforming/differentiating medium.

17. The method according to claim 1, which does not use specific antibody detection of cells.

18. A method of obtaining a homogeneous population of single cell-derived clonal multipotent bone marrow cells based on cell density from a biological sample of bone marrow, comprising:
 (i) allowing the biological sample to settle by gravity in a first container producing a first supernatant of lower density cells;
 (ii) transferring the first supernatant directly without undergoing centrifugation to a second container of growth medium and allowing cells to settle to the bottom producing a second supernatant of lower density cells;
 (iii) transferring the second supernatant directly without undergoing centrifugation to a third container of growth medium and allowing cells to settle to the bottom, producing a third supernatant of lower density cells;
 (iv) transferring the third supernatant directly without undergoing centrifugation to a fourth container of growth medium and allowing cells to settle to the bottom, producing a fourth supernatant of lower density cells;
 (v) transferring the fourth supernatant directly without undergoing centrifugation to another container of growth medium and allowing cells to settle to the bottom, producing another supernatant of lower density cells;
 (vi) allowing single-cell derived colonies to appear on the bottom of the container of step (v);
 (vii) isolating the single-cell derived colonies; and
 (viii) expanding cells from the single-cell derived colonies in a further other container of growth medium to obtain the homogeneous population of single cell-derived clonal multipotent bone marrow cells.

19. The method according to claim 18, wherein the cells are settled for one day in step (v).

20. The method according to claim 18, wherein the isolated cells from the supernatant are expanded in a container.

21. The method according to claim 18, wherein the container has a flat bottom.

22. The method according to claim 18, wherein the container is coated with a cell adhesive agent.

23. The method according to claim 22, wherein the cell adhesive agent comprises a polymer of any charged amino acids.

24. The method according to claim 23, wherein the cell adhesive agent is collagen, polylysine, polyarginine, polyaspartate, polyglutamate, or a combination thereof.

25. The method according to claim 18, comprising contacting the isolated cells with a connective tissue cell transforming/differentiating medium, thereby forming mesoderm lineage cells.

26. The method according to claim 25, wherein the mesoderm lineage cells are connective tissue cells.

27. The method according to claim 26, wherein the connective tissue cells are chondrocytes, and the transforming/differentiating medium is chondrocyte transforming/differentiating medium.

28. The method according to claim 26, wherein the connective tissue cells are adipocytes, and the transforming/differentiating medium is adipocyte transforming/differentiating medium.

29. The method according to claim 26, wherein the connective tissue cells are osteocytes, and the transforming/differentiating medium is osteocyte transforming/differentiating medium.

30. The method according to claim 18, comprising contacting the isolated cells in with an ectoderm tissue cell transforming/differentiating medium thereby forming ectoderm lineage cells.

31. The method according to claim 30, wherein the ectoderm lineage cells are neural tissue cells, and the transforming/differentiating medium is neural tissue transforming/differentiating medium.

32. The method according to claim 18, comprising contacting the isolated cells with an endoderm tissue cell transforming/differentiating medium thereby forming endoderm lineage cells.

33. The method according to claim 32, wherein the endoderm lineage cells are hepatogenic tissue cells, and the transforming/differentiating medium is hepatogenic tissue cell transforming/differentiating medium.

34. The method according to claim 18, which does not use specific antibody detection of cells.

35. A method of obtaining a homogeneous population of single cell-derived clonal multipotent bone marrow cells based on cell density from a biological sample of bone marrow, comprising:
(i) allowing the biological sample to settle by gravity in a first container producing a first supernatant of lower density cells;
(ii) transferring the first supernatant directly without undergoing centrifugation to a second container of growth medium and allowing cells to settle to the bottom producing a second supernatant of lower density cells;
(iii) transferring the second supernatant directly without undergoing centrifugation to a third container of growth medium and allowing cells to settle to the bottom, producing a third supernatant of lower density cells;
(iv) transferring the third supernatant directly without undergoing centrifugation to a fourth container of growth medium and allowing cells to settle to the bottom, producing a fourth supernatant of lower density cells;
(v) transferring the fourth supernatant directly without undergoing centrifugation to a fifth container of growth medium and allowing cells to settle to the bottom, producing a fifth supernatant of lower density cells;
(vi) transferring the fifth supernatant directly without undergoing centrifugation to another container of growth medium and allowing cells to settle to the bottom, producing another supernatant of lower density cells;
(vii) allowing single-cell derived colonies to appear on the bottom of the container of step (vi);
(viii) isolating the single-cell derived colonies; and
(ix) expanding cells from the single-cell derived colonies in a further other container of growth medium to obtain the homogeneous population of single cell-derived clonal multipotent bone marrow cells.

36. The method according to claim 35, wherein the cells are settled for one day in step (vi).

37. The method according to claim 35, wherein the isolated cells from the supernatant are expanded in a container.

38. The method according to claim 35, wherein the container has a flat bottom.

39. The method according to claim 35, wherein the container is coated with a cell adhesive agent.

40. The method according to claim 39, wherein the cell adhesive agent comprises a polymer of any charged amino acids.

41. The method according to claim 40, wherein the cell adhesive agent is collagen, polylysine, polyarginine, polyaspartate, polyglutamate, or a combination thereof.

42. The method according to claim 35, comprising contacting the isolated cells with a connective tissue cell transforming/differentiating medium, thereby forming mesoderm lineage cells.

43. The method according to claim 42, wherein the mesoderm lineage cells are connective tissue cells.

44. The method according to claim 43, wherein the connective tissue cells are chondrocytes, and the transforming/differentiating medium is chondrocyte transforming/differentiating medium.

45. The method according to claim 43, wherein the connective tissue cells are adipocytes, and the transforming/differentiating medium is adipocyte transforming/differentiating medium.

46. The method according to claim 43, wherein the connective tissue cells are osteocytes, and the transforming/differentiating medium is osteocyte transforming/differentiating medium.

47. The method according to claim 35, comprising contacting the isolated cells in with an ectoderm tissue cell transforming/differentiating medium thereby forming ectoderm lineage cells.

48. The method according to claim 47, wherein the ectoderm lineage cells are neural tissue cells, and the transforming/differentiating medium is neural tissue transforming/differentiating medium.

49. The method according to claim 35, comprising contacting the isolated cells with an endoderm tissue cell transforming/differentiating medium thereby forming endoderm lineage cells.

50. The method according to claim 49, wherein the endoderm lineage cells are hepatogenic tissue cells, and the transforming/differentiating medium is hepatogenic tissue cell transforming/differentiating medium.

51. The method according to claim 35, which does not use specific antibody detection of cells.

* * * * *

SEQUENCE LISTING

<160> NUMBER OF SEQ ID NOS: 12

<210> SEQ ID NO 1
<211> LENGTH: 22
<212> TYPE: DNA
<213> ORGANISM: Artificial
<220> FEATURE:
<223> OTHER INFORMATION: Primer

<400> SEQUENCE: 1
aagatggtcc caaaggtgct cg                                           22

<210> SEQ ID NO 2
<211> LENGTH: 22
<212> TYPE: DNA
<213> ORGANISM: Artificial
<220> FEATURE:
<223> OTHER INFORMATION: primer

<400> SEQUENCE: 2
agcttctcct ctgtctcctt gc                                           22

<210> SEQ ID NO 3
<211> LENGTH: 23
<212> TYPE: DNA
<213> ORGANISM: Artificial
<220> FEATURE:
<223> OTHER INFORMATION: primer

<400> SEQUENCE: 3
ctaggcatca cctgtgccat acc                                          23

<210> SEQ ID NO 4
<211> LENGTH: 24
<212> TYPE: DNA
<213> ORGANISM: Artificial
<220> FEATURE:
<223> OTHER INFORMATION: primer

<400> SEQUENCE: 4
cgtgaccagt tcatcagatt catc                                         24

<210> SEQ ID NO 5
<211> LENGTH: 21
<212> TYPE: DNA
<213> ORGANISM: Artificial
<220> FEATURE:
<223> OTHER INFORMATION: primer

<400> SEQUENCE: 5
gctgttatgg gtgaaactct g                                            21

<210> SEQ ID NO 6
<211> LENGTH: 21
<212> TYPE: DNA
<213> ORGANISM: Artificial
<220> FEATURE:
<223> OTHER INFORMATION: primer

<400> SEQUENCE: 6
ataaggtgga gatgcaggct c                                              21

<210> SEQ ID NO 7
<211> LENGTH: 22
<212> TYPE: DNA
<213> ORGANISM: Artificial
<220> FEATURE:
<223> OTHER INFORMATION: primer

<400> SEQUENCE: 7
aactccctca agattgtcag ca                                             22

<210> SEQ ID NO 8
<211> LENGTH: 21
<212> TYPE: DNA
<213> ORGANISM: Artificial
<220> FEATURE:
<223> OTHER INFORMATION: primer

<400> SEQUENCE: 8
tccaccaccc tgttgcttgt a                                              21

<210> SEQ ID NO 9
<211> LENGTH: 22
<212> TYPE: DNA
<213> ORGANISM: Artificial
<220> FEATURE:
<223> OTHER INFORMATION: primer

<400> SEQUENCE: 9
gagcgcaaag actacctgaa ga                                             22

<210> SEQ ID NO 10
<211> LENGTH: 23
<212> TYPE: DNA
<213> ORGANISM: Artificial
<220> FEATURE:
<223> OTHER INFORMATION: primer

<400> SEQUENCE: 10
cagcgatttc tatatccaga gcc                                            23

<210> SEQ ID NO 11
<211> LENGTH: 24
<212> TYPE: DNA
<213> ORGANISM: Artificial
<220> FEATURE:
<223> OTHER INFORMATION: primer

<400> SEQUENCE: 11
tgcagccaaa gtgaagaggg aaga                                           24

<210> SEQ ID NO 12
<211> LENGTH: 24
<212> TYPE: DNA
<213> ORGANISM: Artificial
<220> FEATURE:
<223> OTHER INFORMATION: primer

```
<400> SEQUENCE: 12
catagcgagc agcccaaaga agaa                                      24
```